(12) United States Patent
Athanasiou

(10) Patent No.: US 11,922,633 B2
(45) Date of Patent: Mar. 5, 2024

(54) REAL-TIME LUMEN DISTANCE CALCULATION BASED ON THREE-DIMENSIONAL (3D) A-LINE SIGNAL DATA

(71) Applicant: Canon U.S.A., Inc., Melville, NY (US)

(72) Inventor: Lampros Athanasiou, Medford, MA (US)

(73) Assignee: Canon U.S.A., Inc., Melville, NY (US)

( * ) Notice: Subject to any disclaimer, the term of this patent is extended or adjusted under 35 U.S.C. 154(b) by 66 days.

(21) Appl. No.: 17/354,877

(22) Filed: Jun. 22, 2021

(65) Prior Publication Data

US 2021/0407098 A1    Dec. 30, 2021

Related U.S. Application Data

(60) Provisional application No. 63/046,495, filed on Jun. 30, 2020.

(51) Int. Cl.
*G06T 7/13* (2017.01)
*G06T 7/136* (2017.01)
*G06T 7/168* (2017.01)

(52) U.S. Cl.
CPC ............... *G06T 7/13* (2017.01); *G06T 7/136* (2017.01); *G06T 7/168* (2017.01);
(Continued)

(58) Field of Classification Search
CPC ................ A61B 5/0066; A61B 5/6852; G06T 2207/10101; G06T 2207/20028;
(Continued)

(56) References Cited

U.S. PATENT DOCUMENTS 6,763,261 B2    7/2004 Casscells, III et al.
7,366,376 B2    4/2008 Shishkov et al.
(Continued)

FOREIGN PATENT DOCUMENTS

WO    2016/015052 A1    1/2016
WO    2016/144878 A1    9/2016

OTHER PUBLICATIONS

K. Sihan et al., "Fully Automatic Three-Dimensional Quantitative Analysis of Intracoronary Optical Coherence Tomography: Method and Validation", Catheter. and Cardiovasc. Interv., vol. 74, No. 7, pp. 1058-1065, Jun. 2009.
(Continued)

*Primary Examiner* — Zhiyu Lu
(74) *Attorney, Agent, or Firm* — Canon U.S.A., Inc. I.P. Division

(57) ABSTRACT

One or more devices, systems, methods, and storage mediums for optical imaging medical devices, such as, but not limited to, Optical Coherence Tomography (OCT), single mode OCT, and/or multi-modal OCT apparatuses and systems, and methods and storage mediums for use with same, for calculating lumen distance(s), including based on real-time A-line signal(s), are provided herein. Examples of applications include imaging, evaluating and diagnosing biological objects, such as, but not limited to, for Gastro-intestinal, cardio and/or ophthalmic applications, and being obtained via one or more optical instruments, such as, but not limited to, optical probes, catheters, capsules and needles (e.g., a biopsy needle). Fast A-line lumen segmentation methods, which can be applied real-time to a whole arterial pullback, and devices, systems, and storage mediums for use with same, are provided herein. Techniques provided herein also improve processing efficiency and
(Continued)

decrease calculations while achieving measurements that are more precise.

20 Claims, 22 Drawing Sheets

(52) U.S. Cl.
CPC .............. *G06T 2207/10101* (2013.01); *G06T 2207/20028* (2013.01); *G06T 2207/20182* (2013.01); *G06T 2207/30021* (2013.01); *G06T 2207/30101* (2013.01)

(58) Field of Classification Search
CPC . G06T 2207/20182; G06T 2207/30021; G06T 2207/30041; G06T 2207/30101; G06T 7/13; G06T 7/136; G06T 7/168
See application file for complete search history.

(56) References Cited

U.S. PATENT DOCUMENTS

| | | | |
|---|---|---|---|
| 7,843,572 B2 | 11/2010 | Tearney et al. | |
| 7,872,759 B2 | 1/2011 | Tearney et al. | |
| 7,889,348 B2 | 2/2011 | Tearney et al. | |
| 8,289,522 B2 | 10/2012 | Tearney et al. | |
| 8,478,387 B2 | 7/2013 | Xu | |
| 8,676,013 B2 | 3/2014 | Bouma et al. | |
| 8,831,321 B1 | 9/2014 | Elbasiony | |
| 8,928,889 B2 | 1/2015 | Tearney et al. | |
| 9,087,368 B2 | 7/2015 | Tearney et al. | |
| 9,138,147 B2 | 9/2015 | Schmitt et al. | |
| 9,173,591 B2 | 11/2015 | Elbasiony et al. | |
| 9,332,942 B2 | 5/2016 | Jaffer et al. | |
| 9,557,154 B2 | 1/2017 | Tearney et al. | |
| 9,659,375 B2 | 5/2017 | Zagrodsky et al. | |
| 10,109,058 B2 | 10/2018 | Ambwani et al. | |
| 10,713,786 B2 | 7/2020 | Ambwani et al. | |
| 2010/0092389 A1 | 4/2010 | Jaffer | |
| 2011/0071404 A1 | 3/2011 | Schmitt et al. | |
| 2011/0292400 A1 | 12/2011 | Fleming et al. | |
| 2012/0101374 A1 | 4/2012 | Tearney et al. | |
| 2014/0024930 A1 | 1/2014 | Furuichi et al. | |
| 2014/0257087 A1* | 9/2014 | Elbasiony | A61B 5/0084 600/424 |
| 2014/0276011 A1 | 9/2014 | Schmitt et al. | |
| 2015/0320317 A1 | 11/2015 | Furuichi et al. | |
| 2016/0022208 A1 | 1/2016 | Gopinath | |
| 2016/0228097 A1 | 8/2016 | Jaffer et al. | |
| 2016/0335766 A1 | 11/2016 | Ambwani et al. | |
| 2017/0024532 A1 | 1/2017 | Gopinath et al. | |
| 2017/0135584 A1 | 5/2017 | Tearney et al. | |
| 2018/0003481 A1 | 1/2018 | Yamada et al. | |
| 2018/0045501 A1 | 2/2018 | Elmaanaoui | |
| 2019/0102906 A1* | 4/2019 | Kunio | A61B 5/6852 |
| 2019/0298174 A1 | 10/2019 | Watanabe | |
| 2019/0374109 A1 | 12/2019 | Wu et al. | |
| 2020/0085285 A1 | 3/2020 | Yamada | |
| 2021/0077037 A1 | 3/2021 | Kunio | |
| 2021/0121132 A1 | 4/2021 | Watanabe et al. | |
| 2021/0174125 A1 | 6/2021 | Zhang | |

OTHER PUBLICATIONS

S. Tsantis, et al., "Automatic vessel lumen segmentation and stent strut detection in intravascular optical coherence tomography", Med. Phys., vol. 39, No. 1, pp. 503-513, Jan. 2012.

G. J. Ughi, et al., "Automatic segmentation of in-vivo intra-coronary optical coherence tomography images to assess stent strut apposition and coverage", Int. J. Cardiovasc. Imaging, vol. 28, No. 2, pp. 229-241, Feb. 2012.

G. J. Ughi, et al., "Fully automatic three-dimensional visualization of intravascular optical coherence tomography images: methods and feasibility in vivo", Biomedical Optics Express, vol. 3, No. 12, pp. 3291-3303, Dec. 1, 2012.

L. Athanasiou, et al., "Optimized computer-aided segmentation and 3D reconstruction using intracoronary optical coherence tomography", IEEE J. Biomed. Health Informatics, vol. 22, No. 4, pp. 1168-1176, Jul. 2018 (26 pages in PDF).

* cited by examiner

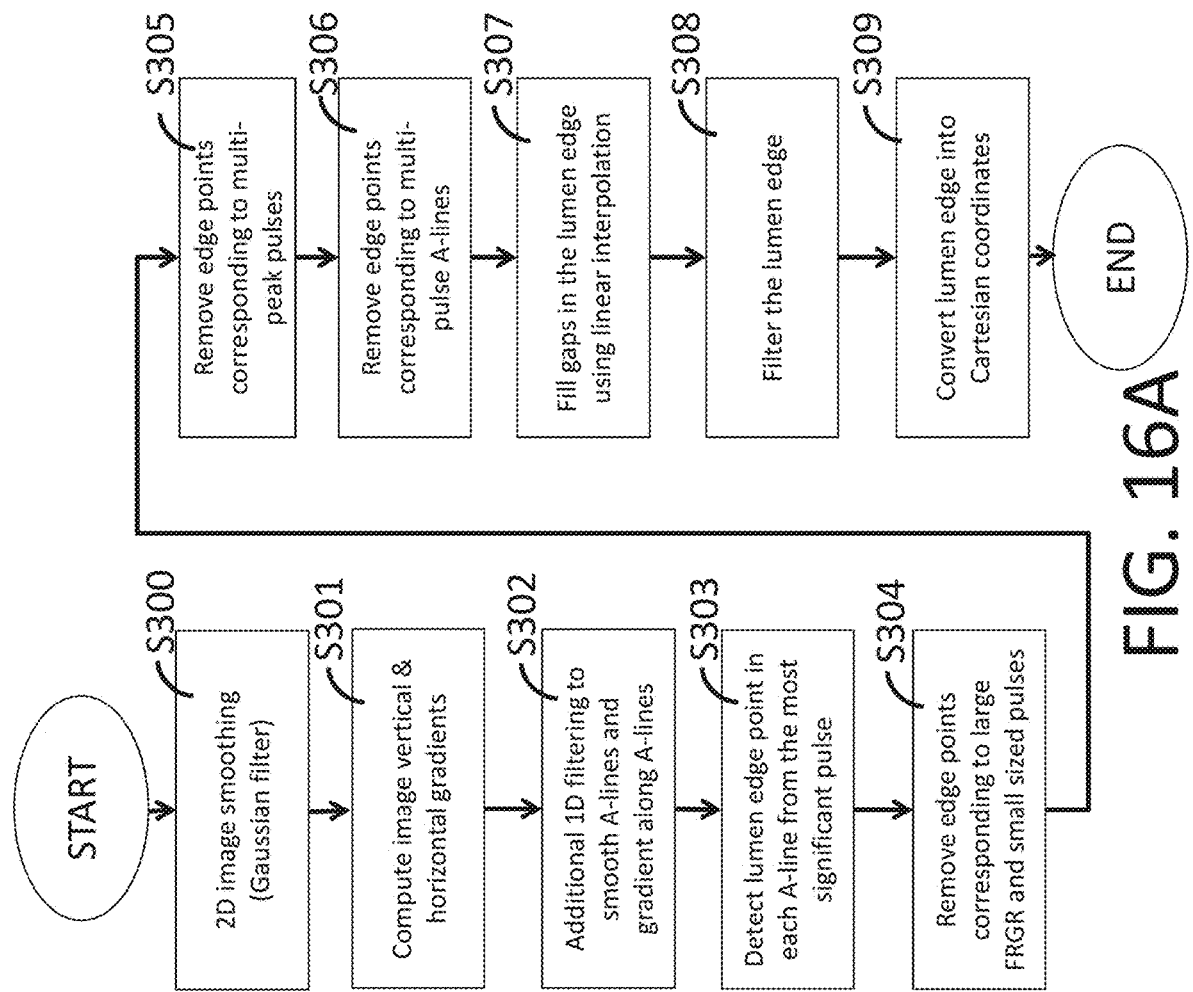

REAL-TIME LUMEN DISTANCE CALCULATION BASED ON THREE-DIMENSIONAL (3D) A-LINE SIGNAL DATA

CROSS-REFERENCE TO RELATED APPLICATION(S)

This application relates, and claims priority, to U.S. Patent Application Ser. No. 63/046,495, filed Jun. 30, 2020, the entire disclosure of which is incorporated by reference herein in its entirety.

FIELD OF THE INVENTION

This present disclosure generally relates to computer imaging and/or to the field of optical imaging, particularly to devices, systems, methods, and storage mediums for using multiple imaging modalities, such as, but not limited to, Optical Coherence Tomography (OCT), Multi-mode OCT (MMO-OCT), near-infrared auto-fluorescence (NIRAF), near-infrared fluorescence (NIRF), etc. Examples of OCT applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring viscosity of, a sample or object in application(s) using an apparatus or system that uses and/or controls multiple imaging modalities are discussed herein.

BACKGROUND OF THE INVENTION

Fiber optic catheters and endoscopes have been developed to access to internal organs. For example in cardiology, OCT has been developed to see depth resolved images of vessels with a catheter. The catheter, which may include a sheath, a coil and an optical probe, may be navigated to a coronary artery.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

During vascular diagnosis and intervention procedures, such as Percutaneous Coronary Intervention (PCI), users of optical coherence tomography (OCT) sometimes have difficulty understanding the tomography image in correlation with other modalities because of an overload of information, which causes confusion in image interpretation.

PCI has been improved using intravascular imaging modalities, such as optical coherence tomography (OCT) and near infrared auto-fluorescence OCT (NIRAF-OCT), which provides additional information about the atherosclerotic tissue that auto-fluoresces the near infrared light.

However, due to catheter or probe movement, the intensity of the NIRAF value is highly dependent on, or is sensitive to, the position of the catheter or probe (e.g., the closer to the lumen the catheter or probe is, the higher the intensity is; NIRAF signal is affected by the distance of the moving catheter to lumen border; etc.). Current methods were developed for detecting the lumen border in OCT images. However, such methods are not processing directly the A-lines of the OCT image and/or do not perform measurements on the A-lines, and the methods either cannot be applied real-time or fail to detect the lumen borders in all the images of an OCT pullback. Such methods cannot provide reliable measurements for the whole OCT pullback due to the presence of imaging artifacts.

As such, there is a need for the NIRAF signal to be adjusted according to the distance of the signal source to the lumen border, and there is a need for a real time, efficient/quick/fast distance calculation of each A-line (collected signal) to the lumen border that may be employed for a robust signal correction. Indeed, there is a need to provide reliable measurements for the whole OCT pullback.

Accordingly, it would be desirable to provide at least one imaging or optical device, system, method, and storage medium for using, controlling, and/or emphasizing one or more multiple imaging modalities, for example, by using a method or methods that adjust a NIRAF signal according to the distance of the signal source to the lumen border, that provide a real time, efficient/quick/fast distance calculation of each A-line (collected signal) to the lumen border for signal correction, and/or that provide reliable measurements for the whole OCT pullback.

SUMMARY OF THE INVENTION

Accordingly, it is a broad object of the present disclosure to provide imaging (e.g., OCT, NIRF, NIRAF, etc.) apparatuses, systems, methods and storage mediums for using and/or controlling real-time lumen distance calculation(s) based on three-dimensional (3D) A-line signal data. It is also a broad object of the present disclosure to provide OCT devices, systems, methods and storage mediums using an interference optical system, such as an interferometer (e.g., SD-OCT, SS-OCT, etc.).

One or more embodiments provide at least one fast A-line lumen segmentation method, which may be applied efficiently and/or in real-time to an arterial pullback (e.g., a whole arterial pullback, a whole pullback, etc.).

By processing A-line cross sections, the computational time may be essentially decreased allowing real time calculations in one or more embodiments: only 2% of the total frames may be processed by the one or more image segmentation algorithms or methods in one or more embodiments; a predetermined percentage of total frames may be processed only by one or more image segmentation methods or algorithms (e.g., not all of the total frames need to be processed in one or more embodiments, less than all of the total frames may be processed in one or more embodiments, etc.); etc. By applying the method(s) directly to the A-lines, more precise measurements may be achieved avoiding the Cartesian to Polar transformation in one or more embodiments. By applying the global correction to the A-line border, the lumen border in all A-lines may be automatically improved in one or more embodiments. By applying the global correction to the lumen border of the OCT frames in one or more embodiments, all the lumen borders may be automatically corrected, and the new distances may be calculated.

In one or more embodiments, a method for processing intravascular imaging signal data may include: detecting vessel lumen borders using intravascular imaging signal; calculating fast the distance from the lumen border to the catheter or probe using the depicting the lumen border in each 2D OCT frame allowing for a global correction; allowing the detection of the vessel lumen borders in all the pullback data including the ones having noise and/or branch areas (or other predetermined factors); and allowing for a more detailed detection in a case where the user specifies a smaller angle interval than the default.

Lumen edge detection in OCT imaging may be susceptible to artifacts, which correspond to many features, including, but not limited to: stent strut(s), guide wire(s), image brightness variation due to imaging angle, sheath reflections, an irregular shape of a vessel cross section, etc. Certain applications of OCT, such as multimodality OCT (MMOCT) systems/apparatuses, may use lumen edge detection to correct near-infrared autofluorescence (NIRAF) or near-infrared fluorescence (NIRF) signal distance attenuation. Preferably, accurate, real-time NIRAF or NIRF imaging uses accurate detection of lumen edge(s) in real-time based on a single frame of an OCT image. See, for example, U.S. Pat. Pub. 2019/0298174, U.S. patent application Ser. No. 16/131,662, and U.S. Pat. Appl. Ser. No. 62/925,655, each of which are herein incorporated by reference in their entireties. Accurately detecting a lumen edge(s) using a single OCT frame helps to improve overall object or target, such as a vessel, measurement accuracy, including for post processing.

In one or more embodiments of the present disclosure, an OCT image is formed in a polar coordinate system from A-lines, for example, as discussed in U.S. Pat. App. No. 62/944,064, filed on Dec. 5, 2019, which is incorporated by reference herein in its entirety. Each A-line includes much information about the imaged object, such as, but not limited to: clear indications of artifacts from metal objects (e.g., stents, stent struts, guide wires, etc.) like narrow signal width and/or sharp rising and falling edges; significant difference in signal intensity and shape for unobstructed soft tissue compared to the sheath reflection and other artifacts like wide signal width and a gentle falling edge. Each A-line represents a cross-sectional 1D sampling of a target, sample, object, etc., such as, but not limited to, a vessel, along a certain view angle. In one or more embodiments, as an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

One or more embodiments of a lumen distance calculation method or algorithm may include one or more of the following: (a) importing the A-lines of an imaging system (e.g., an OCT system); (b) constructing a 3D volume from the A-lines; (c) extracting and segmenting a number of two-dimensional (2D) cross sections of the 3D volume (this leads to a reduction in the method's overall computational time since only those cross sectional frames (e.g., 1-4% of the whole pullback, 2-4% of the whole pullback, 1-2% of the whole pullback, 1-3% of the whole pullback, 2-3% of the whole pullback, etc.) may be segmented by the method/algorithm); (d) finding and connecting edges of segmented objects in each 2D cross section images; (e) translating points (e.g., of the edges of the segmented objects; of the segmented objects in each 2D cross section images; of the segmented objects; etc.) to the corresponding A-line frames, interpolating the missing points in the A-line images, and estimating the lumen border in every A-line of every frame (this step ensures that the lumen points in the A-line segments which correspond to areas having shadows and artifacts may be detected in one or more embodiments); (f) calculating a distance of each point to the catheter/probe and feeding/inputting the distances of each of the points to a NIRAF signal correction method/algorithm; and (g) transforming the detected lumen borders and the corresponding 2D A-line frames from polar to Cartesian coordinates in order for, or to achieve a result of having, the real vessel morphology to be revealed.

The present disclosure describes a means to allow OCT users to focus on the area of interest in all imaging modalities, such as, but not limited to, a tomography image, near-infrared fluorescence (NIRAF) information in carpet view, three-dimensional (3D) rendering of a coronary vessel in a half pipe display, lumen diameter display, longitudinal view, and angiography view. This allows the users to get a full view of the structural vessel information using one modality or multi-modalities and allows configurability of the function for more targeted focus when providing the fast, efficient A-line lumen segmentation method(s).

One or more lumen, stent, or other object detection technique(s) and/or processes may be used in one or more embodiments of the present disclosure, such as, but not limited to, one or more lumen U.S. patent application Ser. No. 16/414,222, filed on May 16, 2019, stent, or other object detection technique(s) and/or processes as discussed in the entire disclosure of which is incorporated by reference herein in its entirety. For example, one or more embodiments of the present disclosure may take advantage of this constraint of having only one lumen edge pixel of interest in each A-line in a cross-sectional image in polar coordinate. By utilizing 1D signal processing techniques to determine this single edge pixel in each A-line, one or more embodiments of the present disclosure simplify the lumen edge detection algorithm and completely eliminate the need of finding global optimal thresholds for the cross-sectional 2D image. This allows each A-line to have its own optimal threshold for best detection result (i.e., total number of A-lines corresponds to number of different thresholds in one image).

In accordance with one or more embodiments of the present disclosure, apparatuses and systems, and methods and storage mediums for A-line distance calculation(s) may operate to characterize biological objects, such as, but not limited to, blood, mucus, tissue, etc.

It should be noted that one or more embodiments of the A-line distance calculation method(s) of the present disclosure may be used in other imaging systems, apparatuses or devices, where images are formed from signal reflection and scattering within tissue sample(s) using a scanning probe. For example, IVUS images may be processed in addition to or instead of OCT images.

One or more embodiments of the present disclosure may be used in clinical application(s), such as, but not limited to, be intervascular imaging, intravascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, one or more technique(s) discussed herein may be employed as or along with features to reduce the cost of at least one of manufacture and maintenance of the one or more apparatuses, devices, systems and storage mediums by reducing or minimizing a number of optical and/or processing components and by virtue of the efficient techniques to cut down cost of use/manufacture of such apparatuses, devices, systems and storage mediums.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other imaging modality technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 16A-16B show are flow diagrams showing respective embodiments of at least two lumen, stent, and/or artifacts detection processes that may be used with one or more embodiments of real-time lumen distance calculation methods and/or techniques in accordance with one or more aspects of the present disclosure;

DETAILED DESCRIPTION OF THE PRESENT INVENTION

Figure 1:
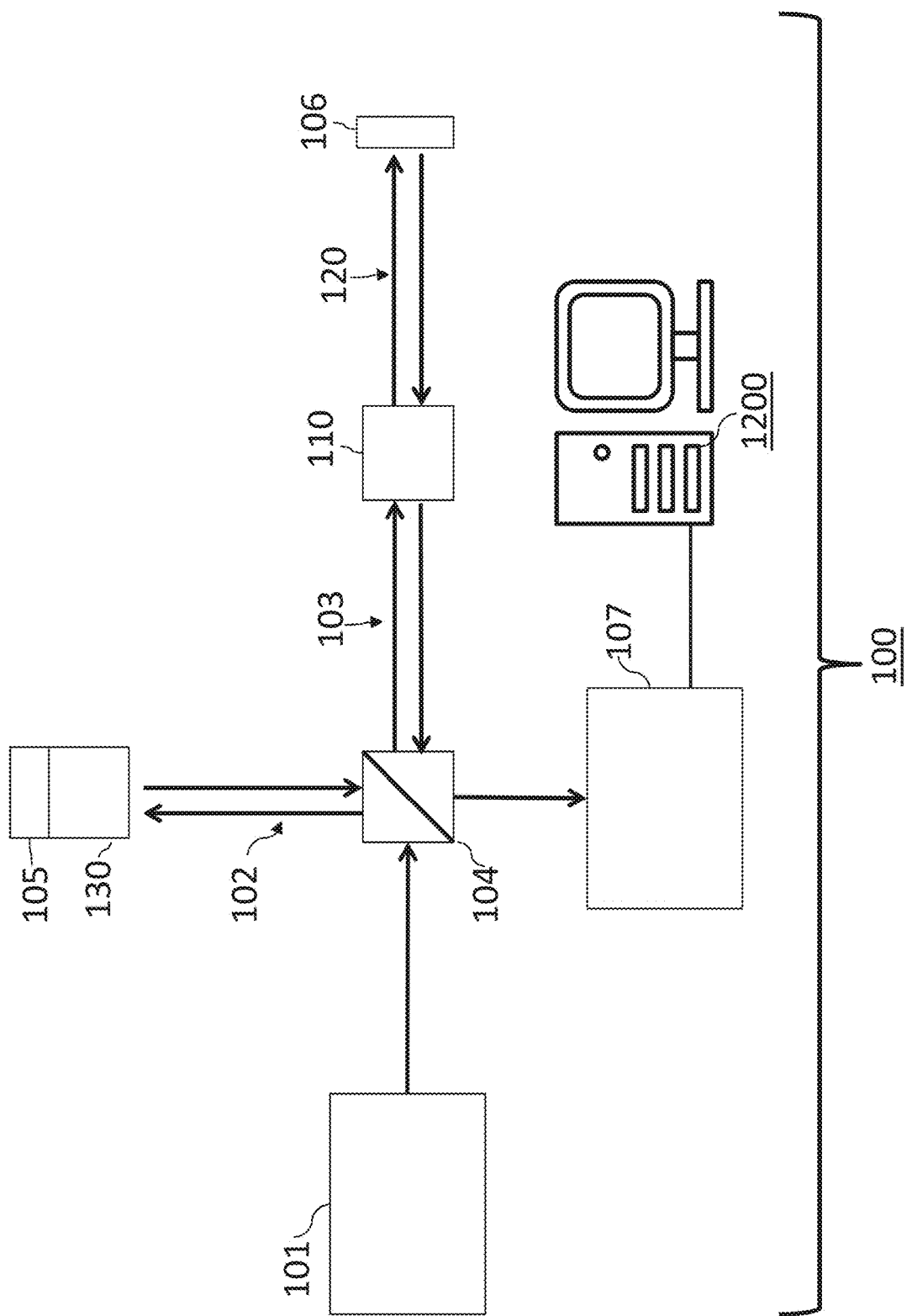
FIG. 1 is a schematic diagram showing at least one embodiment of a system that may be used for performing one or more embodiments of a real-time lumen distance calculation method(s) based on 3D A-line signal data in accordance with one or more aspects of the present disclosure.

One or more devices, systems, methods and storage mediums for characterizing tissue, or an object or sample, using one or more imaging and/or calculation techniques or modalities (such as, but not limited to, OCT, NIRAF, etc.) are disclosed herein. Several embodiments of the present disclosure, which may be carried out by the one or more embodiments of an apparatus, system, method and/or computer-readable storage medium of the present disclosure are described diagrammatically and visually in FIGS. 1 through 22.

One or more embodiments provide at least one fast A-line lumen segmentation method, which may be applied efficiently and/or in real-time to an arterial pullback (e.g., a whole arterial pullback, a whole pullback, etc.).

By processing A-line cross sections, the computational time may be essentially decreased allowing real time calculations in one or more embodiments: only 2% of the total frames may be processed by the one or more image segmentation algorithms or methods in one or more embodiments; a predetermined percentage of total frames may be processed only by one or more image segmentation methods or algorithms (e.g., not all of the total frames need to be processed in one or more embodiments, less than all of the total frames may be processed in one or more embodiments, etc.); etc. By applying the method(s) directly to the A-lines, more precise measurements may be achieved avoiding the Cartesian to Polar transformation in one or more embodiments. By applying the global correction to the A-line border, the lumen border in all A-lines may be automatically improved in one or more embodiments. By applying the global correction to the lumen border of the OCT frames in one or more embodiments, all the lumen borders may be automatically corrected, and the new distances may be calculated.

In one or more embodiments, a method for processing intravascular imaging signal data may include: detecting vessel lumen borders using intravascular imaging signal; calculating fast the distance from the lumen border to the catheter or probe using the depicting the lumen border in each 2D OCT frame allowing for a global correction; allowing the detection of the vessel lumen borders in all the pullback data including the ones having noise and/or branch areas (or other predetermined factors, other factors discussed herein, etc.); and allowing for a more detailed detection in a case where the user specifies a smaller angle interval than the default.

Turning now to the details of the figures, processing intravascular imaging data and/or performing real-time lumen distance calculation(s) may be performed in one or more ways as discussed herein. One or more displays discussed herein may allow a user of the one or more displays to use, control and/or emphasize one or more imaging and/or calculation techniques or modalities, such as, but not limited to, OCT, NIRAF, etc., and may allow the user to use, control, and/or emphasize the one or more imaging techniques or modalities synchronously, and/or may allow the user to perform real-time lumen distance calculation method(s) (including method(s) based on 3D A-line signal data) and/or to process intravascular imaging data.

As shown diagrammatically in FIG. 1, one or more embodiments of a system or apparatus for visualizing, emphasizing and/or controlling one or more imaging modalities, and/or for performing real-time lumen distance calculation method(s) (including method(s) based on 3D A-line signal data) and/or to process intravascular imaging data, of the present disclosure may be involved with one or more predetermined or desired procedures, such as, but not limited to, medical procedure planning and performance.

FIG. 1 shows an OCT system 100 (as referred to herein as "system 100" or "the system 100") which operates to utilize an OCT technique, including, but not limited to, one or more embodiments of allowing the user to use, control, and/or emphasize the one or more imaging techniques or modalities synchronously, and/or allowing the user to perform real-time lumen distance calculation method(s) (including method(s) based on 3D A-line signal data) and/or processing intravascular imaging data techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") 110 and a catheter or probe 120 (as diagrammatically shown in FIGS. 1-2), and the system 100 may interact with a sample or target 106 (e.g., via the catheter/probe 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104, and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit; also referred to herein as a patient interface component (PIC)) 110 and the catheter or probe 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 21 or FIG. 22, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100'', the system 100''', etc.

In accordance with at least one aspect of the present disclosure, a feature of OCT systems is implemented using fiber optics. As aforementioned, one application of an OCT technique of the present disclosure is to use OCT with a catheter or probe 120 as schematically shown in FIGS. 1-2.

Figure 2:
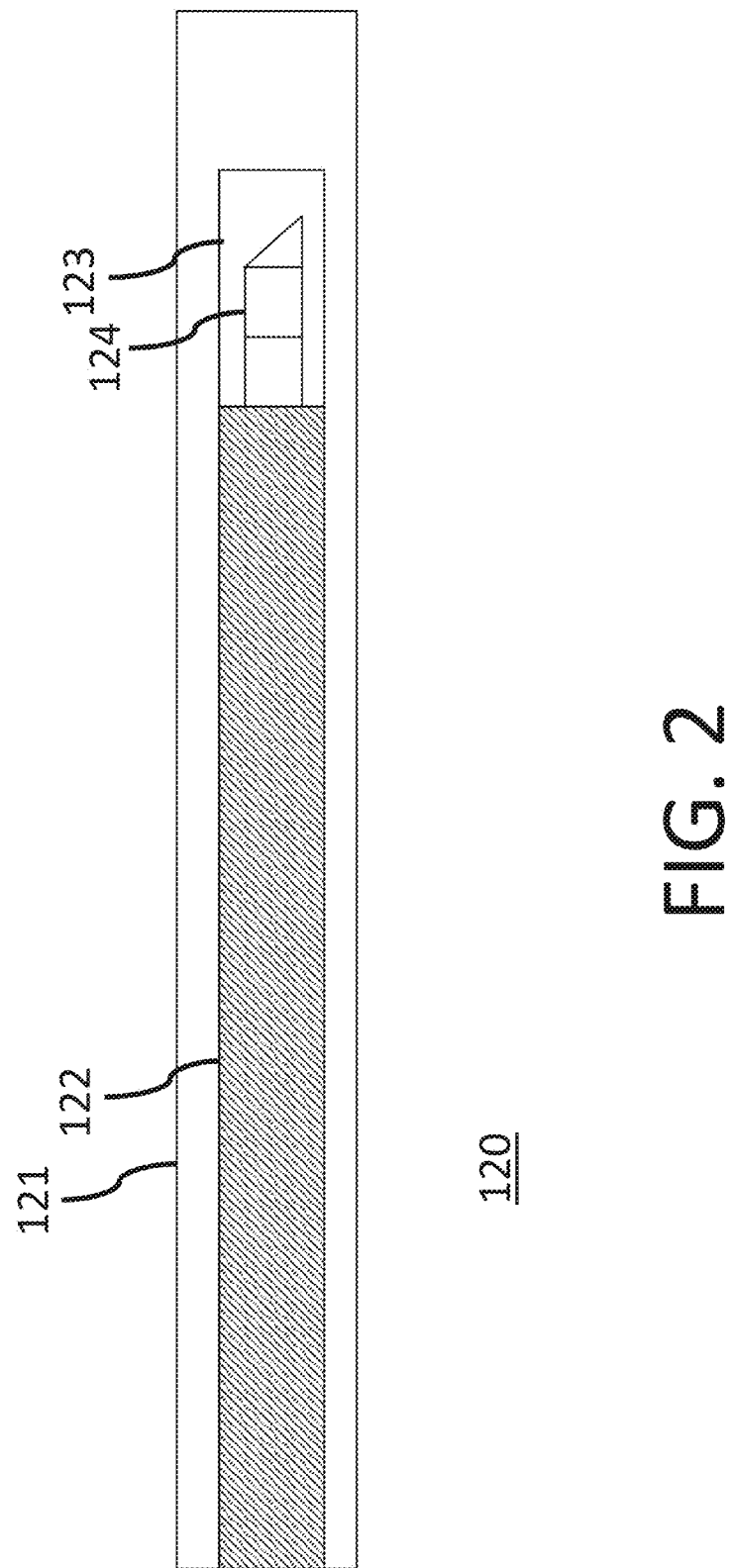
FIG. 2 is a diagram of an embodiment of a catheter or probe that may be used with at least one embodiment of an apparatus, method, or system for performing A-line lumen distance calculation techniques in accordance with one or more aspects of the present disclosure.

FIG. 2 shows an embodiment of the catheter 120 including a sheath 121, a coil 122, a protector 123 and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1-2)), a needle, a capsule, a patient interface unit or component (e.g., the patient interface unit or component 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 21 and/or the console 1200' of FIG. 22 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100'', the system 100''', etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 21 and/or the console 1200' of FIG. 22 as further discussed below). The output of the one or more components of the system 100 (and other systems, such as, but not limited to, the system 100', the system 100", the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100''', etc. as discussed further below) or one or more components thereof are converted to digital signals to be analyzed with a computer, such as, but not limited to, the computer 1200, 1200' (e.g., as shown in FIGS. 1, 17-19, and 21-22). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

In one or more embodiments, one or more imaging and/or processing techniques may be used, such as, but not limited to, various OCT imaging techniques, lumen edge detection, stent strut detection, and/or artifact detection techniques, and other techniques as discussed in at least U.S. Pat. App. No. 62/901,472, which is incorporated by reference herein in its entirety. In one or more embodiments of the present disclosure, an OCT image is formed in a polar coordinate system from A-lines. Each A-line includes much information about the imaged object, such as, but not limited to: clear indications of artifacts from metal objects (e.g., stents, stent struts, guide wires, PIU reflection, catheter/probe reflection, noise artifacts, etc.) like narrow signal width and/or sharp rising and falling edges; significant difference in signal intensity and shape for unobstructed soft tissue compared to the sheath reflection and other artifacts like wide signal width and a gentle falling edge. Each A-line may represent a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In accordance with at least one aspect of the present disclosure and as aforementioned, one or more additional methods for lumen, stent, and/or artifacts detection of OCT images are provided herein and are discussed in U.S. patent application Ser. No. 16/414,222, filed on May 16, 2019, the entire disclosure of which is incorporated by reference herein in its entirety.

Regardless of the approach, a predetermined or determined threshold may be used to detect the most significant pulse that may be corresponding to the lumen edge (in one or more embodiments, the most significant pulse denotes the maximum peak and its associated front edge also named as "major peak/edge"; such data may contain or include artifact edge pixels) in a specific A-line in one or more embodiments. Any pulse above the threshold is an edge pulse of an object candidate. The largest pulse among all the candidates in terms of area under the pulse is considered to be the maximum peak (also referred to herein as the "most significant pulse", or the "major peak/edge", etc.).

One or more embodiments of the present disclosure may minimize, reduce, and/or avoid engagement and disengagement failures and may have a robust means of determining status of probe/catheter engagement to an apparatus or system (e.g., an imaging apparatus, an imaging system, etc.). Knowledge of probe engagement status may be used to communicate status to a user and to allow specific apparatus and/or system functionality and/or to inhibit other apparatus and/or system functionality.

One or more embodiments may obtain a direct analysis and indication of a probe/catheter connection and/or mating process using at least one reliable optical interference signal. One or more embodiments may operate with or without prior knowledge of reflection strength(s) from probe/catheter distal reflections, and preferably do not require such knowledge of the reflection strength(s).

One or more embodiments of the present disclosure may use an OCT signal at a PIU output connector to determine engagement/disengagement status, and/or may use an OCT signal about or for the PIU output connector and a catheter connector to guide an engagement/disengagement process (also referred to herein as an "engagement process" or a "mating step or process").

One or more features of the present disclosure may be employed or exercised using any OCT apparatus and/or system, and may be done so using only minor modifications to the reference arm where an apparatus and/or system uses a single reference arm path, one or more embodiments of a method or technique of the present disclosure may use two reference arm paths or the ability to sufficiently adjust reference arm delay so as to adjust the imaging FOV to be at either the main sample imaging location or at about the system distal-most point (mating location).

One or more embodiments of a system for increasing imaging depth range may include: an OCT system; a reference reflection adjusted so that a reflection from a system mating connector is visible in an imaging field of view; and one or more processors that operate to determine if a catheter/probe is mated to the system mating connector.

Figure 3:
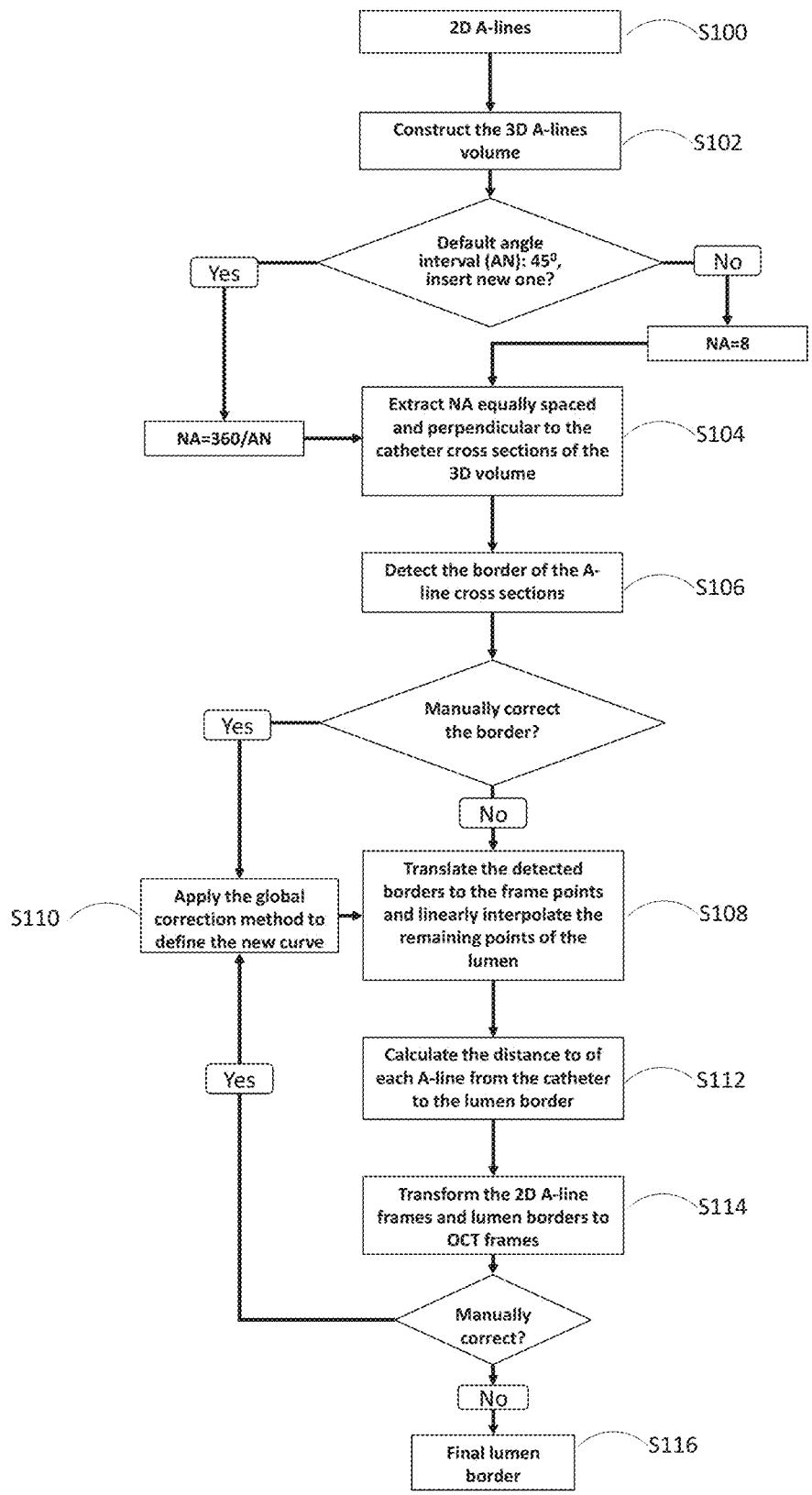
FIG. 3 is a flow diagram of at least one embodiment of an A-line distance calculation method in accordance with one or more aspects of the present disclosure.
Figure 4:
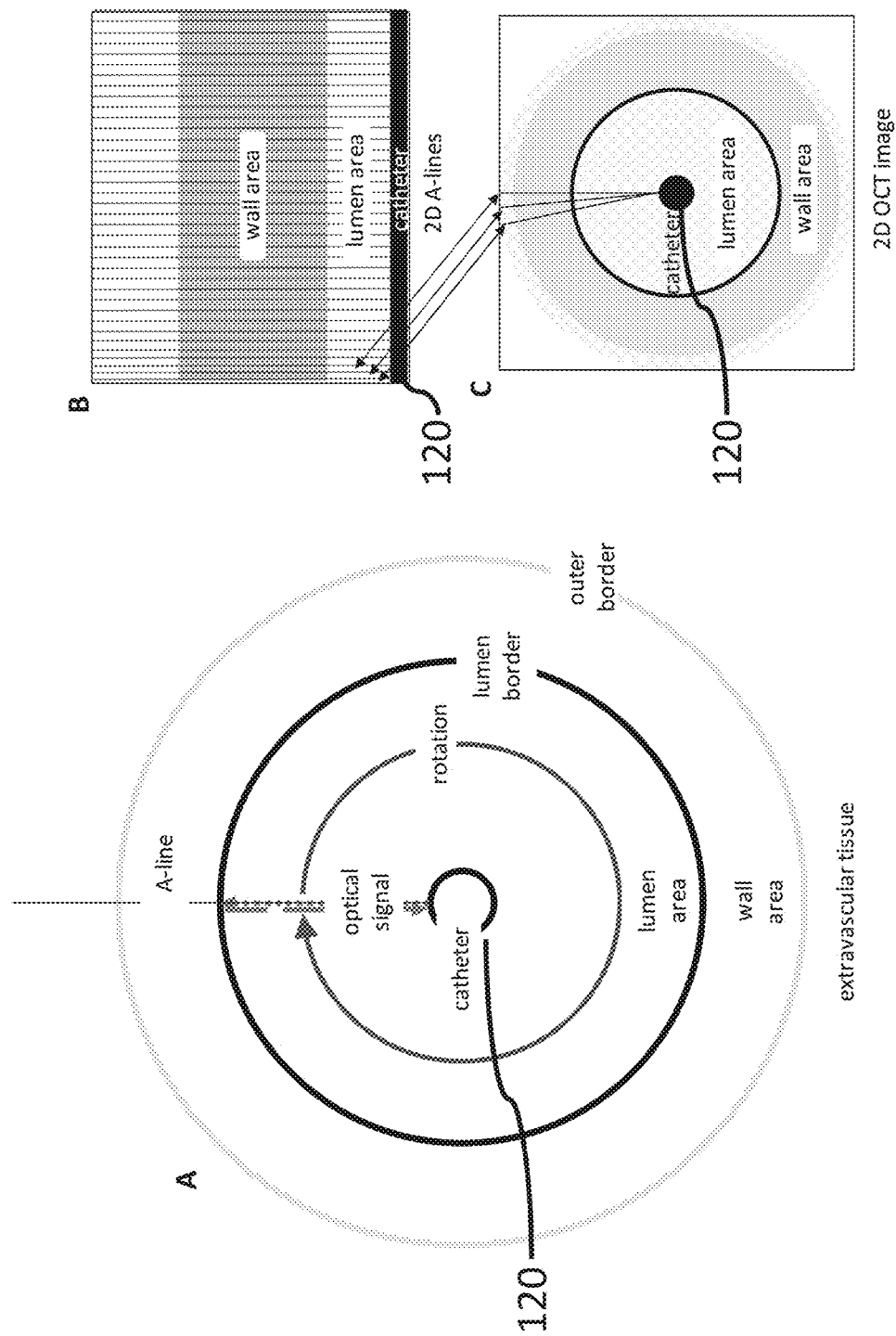
FIG. 4 is a schematic presentation of at least one embodiment example of a correlation between the (A) OCT catheter/probe rotation, (B) A-lines, and (C) an OCT image in accordance with one or more aspects of the present disclosure.
Figure 5:
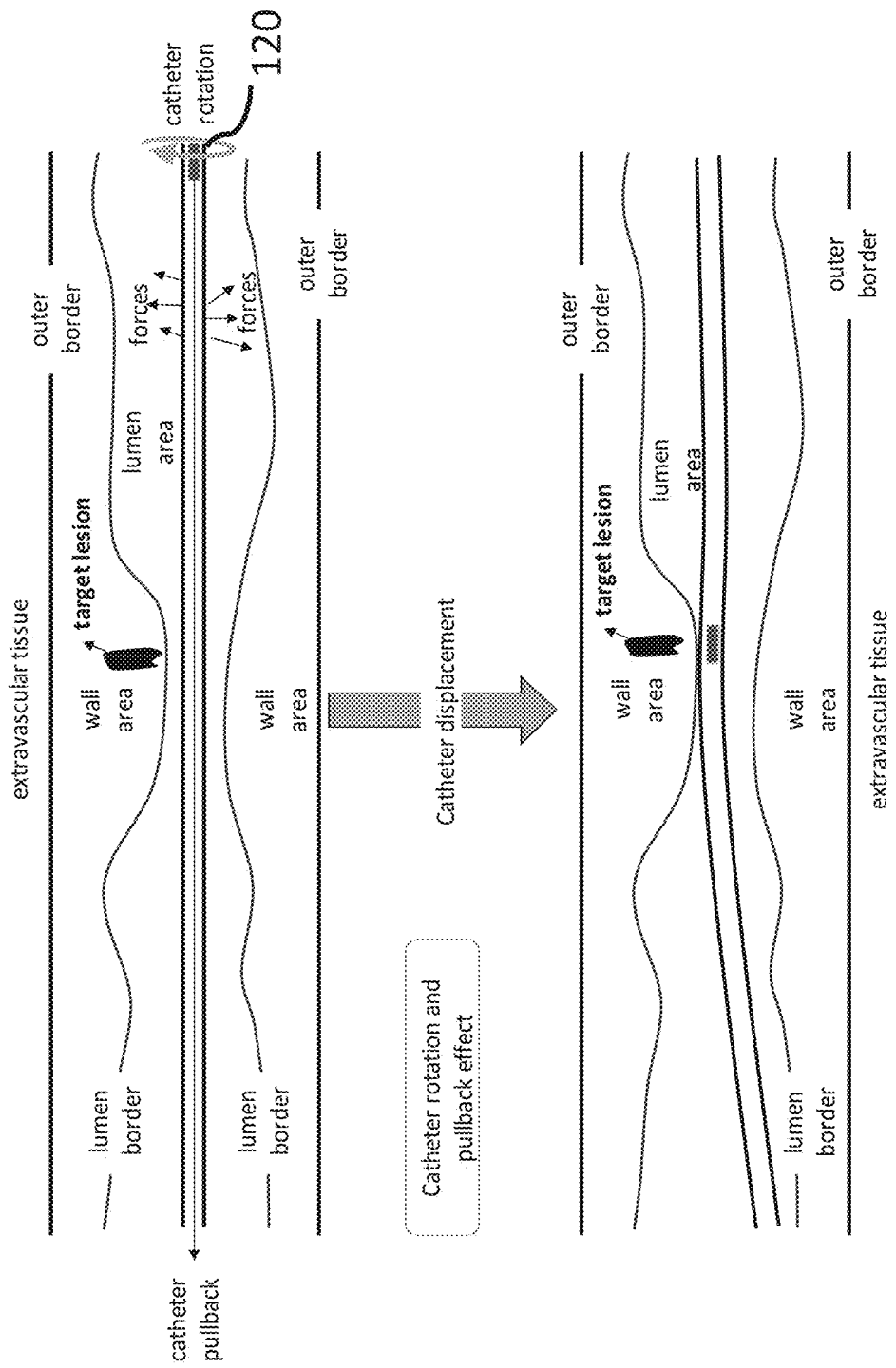
FIG. 5 is a schematic presentation of at least one embodiment example of a catheter or probe displacement phenomenon that may occur when, due to catheter auto-rotation and pullback, different arbitrary forces are moving the catheter or probe along a vessel wall in accordance with one or more aspects of the present disclosure.

Now turning to the details of FIG. 3, at least one embodiment example of an A-line distance calculation method is shown, and at least one embodiment of an overall workflow of the method may include: (i) obtaining or receiving two-dimensional (2D) A-lines, such as, but not limited to sequential blocks of 2D A-lines (see e.g., step S100 in FIG. 3); (ii) constructing a 3D A-line volume matrix from the 2D A-lines (see e.g., step S102 in FIG. 3); (iii) determining whether to give a user a choice to increase or decrease an angle interval (AN) of an OCT image from a default interval (e.g., default may be set to 450 in one or more embodiments); if "Yes", calculate the number of A-lines (NA) to be NA=360/AN, or if "No", set NA to be NA=8, and then proceed to step S104 in FIG. 3; (iv) extracting NA equally spaced and perpendicular to the catheter or probe cross section(s) of or from the 3D A-line volume (see e.g., step S104 in FIG. 3); (v) detecting a border or borders of the A-line cross sections and/or performing segmentation procedure(s) of the 3D A-line cross-section(s) (see e.g., step S106 in FIG. 3); (vi) determining whether to manually correct the border or borders—if "Yes", then applying a global correction method or methods to define a new curve for the cross sectional A-line border or borders (see e.g., step S110 in FIG. 3) and then proceed to step S108 in FIG. 3, or if "No", then proceed to step S108 in FIG. 3; (vii) translating the detected border(s) to frame points and linearly interpolating the remaining points of the lumen (see e.g., step S108 in FIG. 3); (viii) calculating a distance to or of each A-line from the catheter or probe to the lumen border (see e.g., step S112 in FIG. 3); (ix) transforming the 2D A-line frames and lumen borders to OCT frames (or to frames of another set or predetermined imaging modality, or transforming from A-lines to Cartesian coordinates superimposed over their corresponding OCT images (e.g., OCT images having: residual blood, side branches, regular shaped vessel, stented and poor flashing areas, etc.), etc.) (see e.g., step S114 in FIG. 3); (x) determining whether to perform another global correction method or methods; if "Yes", then applying the global correction method or methods (see e.g., arrow returning to step S110 or repeating a method the same as or similar to step S110 to apply the global correction (and/or to steps S110 through S114)) to define a new curve or curves as further discussed below, or, if "No", then complete the transformation step S114 in FIG. 3; and (xi) prepare or determine the final lumen border (see e.g., step S116 in FIG. 3).

One or more steps of the method embodiment of FIG. 3 provide one or more advantages. For example, step S106 of FIG. 3 may achieve faster processing (e.g., segmenting NA images is faster than the whole OCT pullback). By way of another example, the automatic segmentation of step S106 of FIG. 3 may be more precise since less variance is in the 3D A-line cross section than the 2D OCT cross section, so detecting the border of 3D cross sections may be more precise. By way of a further example, step S104 of FIG. 3 may allow the user to increase the segmentation accuracy by choosing more cross sections such that the detail of detection may be chosen by the user. By way of yet another example, step S110 of FIG. 3 may allow the user to correct either the border detection or the lumen detection (e.g., via the drag and drop global correction feature(s) discussed herein), and the pre and post frames of the corrected frame may be automatically corrected. Yet a further example involves A-line distance calculations (e.g., in one or more embodiments of step S108 of FIG. 3) where the A-line distance from the lumen to the catheter or probe (e.g., the catheter or probe 120) may be achieved without any transformation from Cartesian to polar coordinates, such that the accuracy of the computations/processing is improved and the computational time may be decreased.

Figure 6:
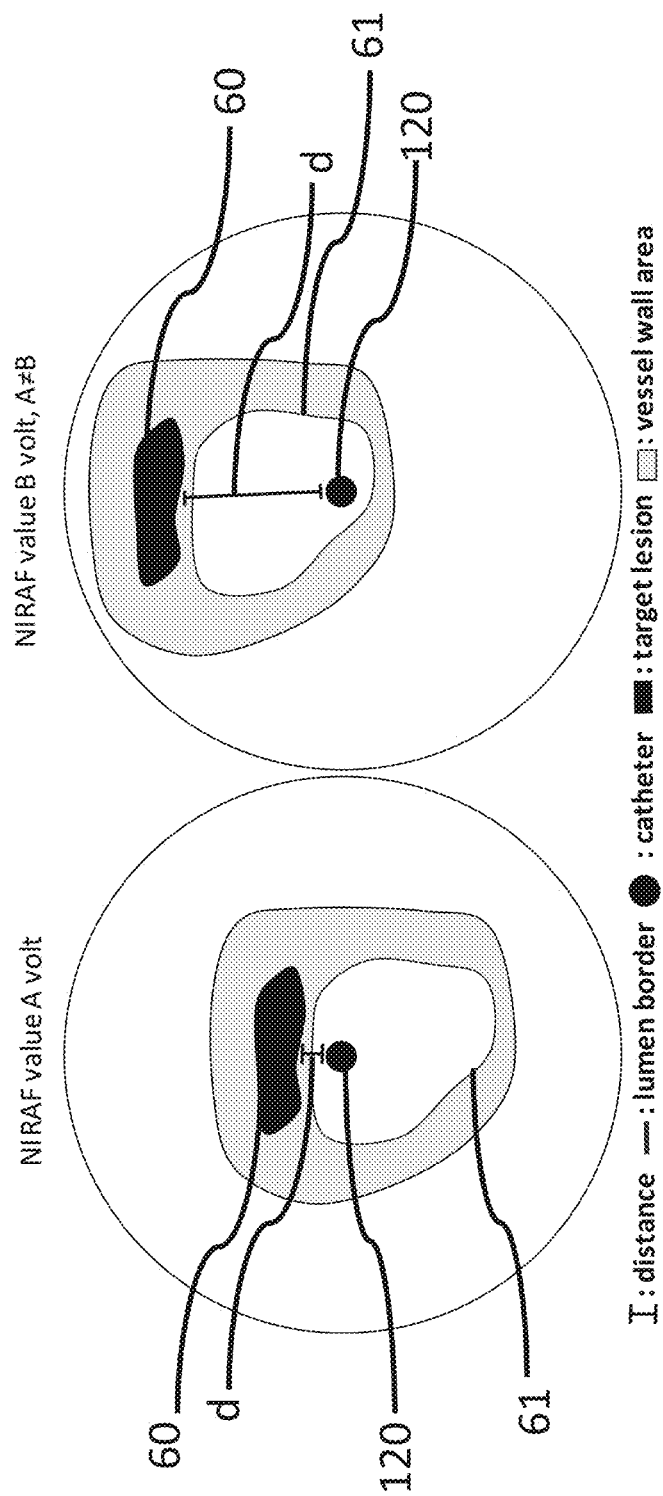
FIG. 6 shows at least one embodiment example of an A-line distance dependable NIRAF value where the NIRAF signal is higher when the catheter or probe is closer to a lumen border in accordance with one or more aspects of the present disclosure.
Figure 7:
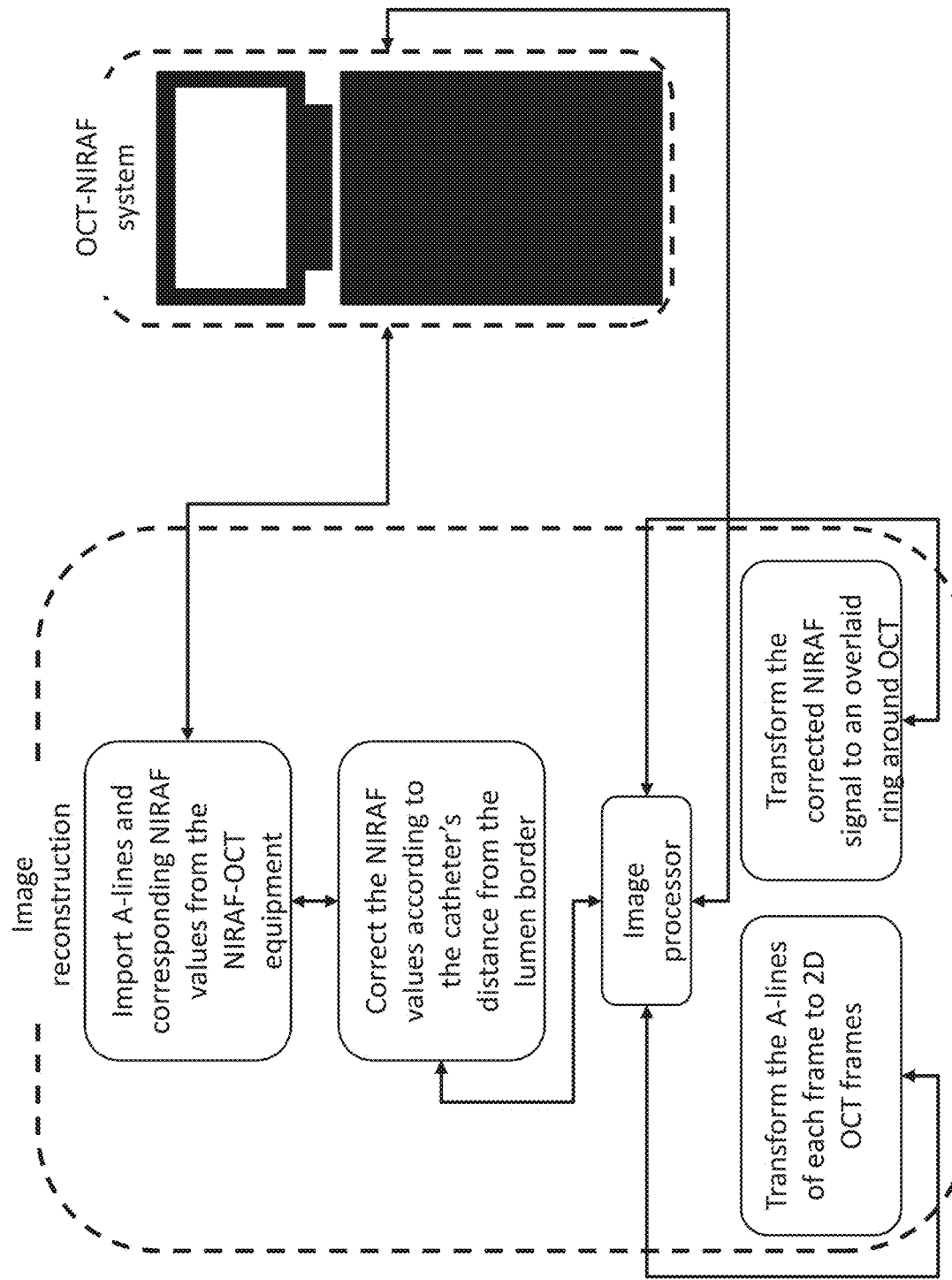
FIG. 7 is a flow diagram of at least one embodiment of an OCT image production using a NIRAF-OCT device or system in accordance with one or more aspects of the present disclosure.

Optical coherence tomography (OCT) may be used to image the structure of the coronary arterial wall. The technology is based on an invasive optical catheter or probe (e.g., the catheter or probe 120) which may be inserted into the coronaries through the femoral artery. In one or more embodiments, the catheter or probe (e.g., the catheter or probe 120) performs a spin around while being simultaneously pullbacked, collecting the reflected optical signals (also referred as "A-lines" herein). Each group of A-lines represent a full spin of the catheter (e.g., the catheter or probe 120) and correspond to a cross section (e.g., 2D OCT frame, a 2D frame of another selected or predetermined imaging modality, etc.) of the artery. However, in order for the arterial morphology to be revealed in one or more embodiments, the A-line group may be transformed to Cartesian coordinates. At least one embodiment of a correlation between the OCT catheter (e.g., the catheter or probe 120) rotation (see e.g., portion A of FIG. 4), A-lines (see e.g., portion B of FIG. 4), and OCT image (see e.g., portion C of FIG. 4) is schematically presented in FIG. 4. In at least one recently developed OCT-NIRAF system embodiment of the present disclosure, for each A-line, the reflected near infrared autofluorescence light (NIRAF) also may be collected and stored in correspondence to the A-lines. However, during the OCT image acquisition, the catheter or probe (e.g., the catheter or probe 120) performs a pullback along the targeted vessel. This movement in combination with auto rotation results of the catheter or probe (e.g., the catheter or probe 120) may result in an arbitrary catheter or probe displacement. Therefore, there is a possibility the same type of lesion may be imaged from a different catheter distance if or in a case where multiple pullbacks are performed on the same vessel. This catheter displacement phenomenon, which is described schematically in FIG. 5, does not only affect the OCT image but also affects the NIRAF values in one or more embodiments. As shown in FIG. 6, the NIRAF intensity of the same lesion 60 varies depending on its relative distance, d, from the catheter (source of signal) (e.g., such as the catheter or probe 120). For example, FIG. 6 illustrates an A-line distance dependable NIRAF value where the NIRAF signal may be higher when the catheter is closer to the lumen border. Therefore, at least one embodiment of an OCT-NIRAF system of the present disclosure applies a correction algorithm to the NIRAF signal in order to provide a more robust NIRAF value estimation. FIG. 7 illustrates a schematic diagram of at least one embodiment of an OCT-NIRAF system where the NIRAF values may be corrected according to the distance of the catheter (e.g., the catheter or probe 120) to the lumen border of each A-line. Since the NIRAF signal is provided simultaneously with the OCT image to the clinical experts, both the lumen to catheter distance algorithm(s) or method(s) and the correction algorithm(s) or method(s) may be applied in real time in one or more embodiments. The OCT-NIRAF system may be any system or apparatus discussed herein, including, but not limited to, system 100, system 100', system 100", system 100''', etc. As shown in FIG. 7, image construction and/or reconstruction may include: (i) importing A-lines and corresponding NIRAF values from the OCT-NIRAF system or equipment; (ii) correcting the NIRAF values according to the catheter's or probe's (e.g., the catheter or probe 120) distance from the lumen border (e.g., the lumen border 61); and (iii) performing image processing (which may include, for example, at least: transforming the A-lines of each frame to 2D OCT frames; transforming the corrected NIRAF signal to an overlaid ring around OCT; etc.).

Figure 8:
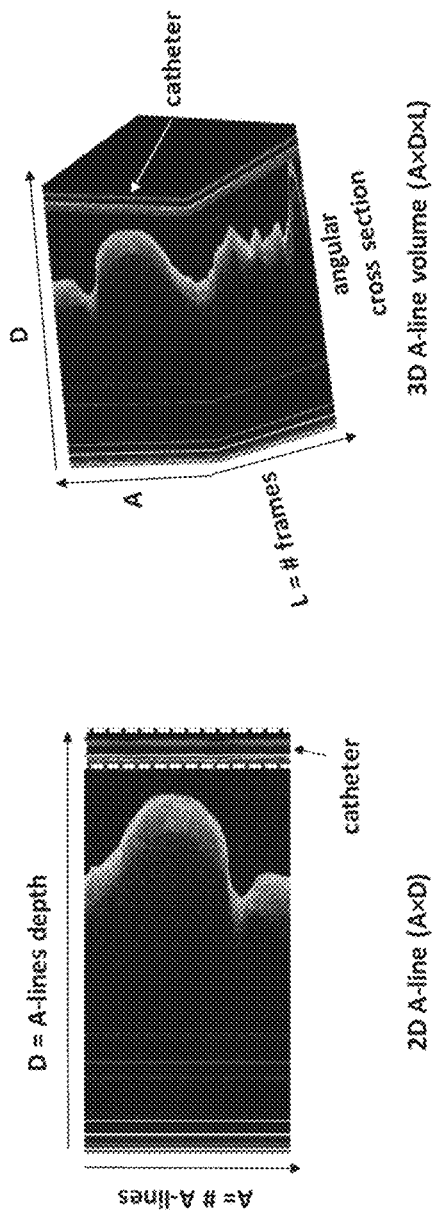
FIG. 8 shows at least one embodiment example of a construction of a 3D A-line volume matrix (right side of FIG. 8; see e.g., step S102 in FIG. 3) from sequential blocks of 2D A-lines (left side of FIG. 8; see e.g., step S100 in FIG. 3) in accordance with one or more aspects of the present disclosure.
Figure 9:
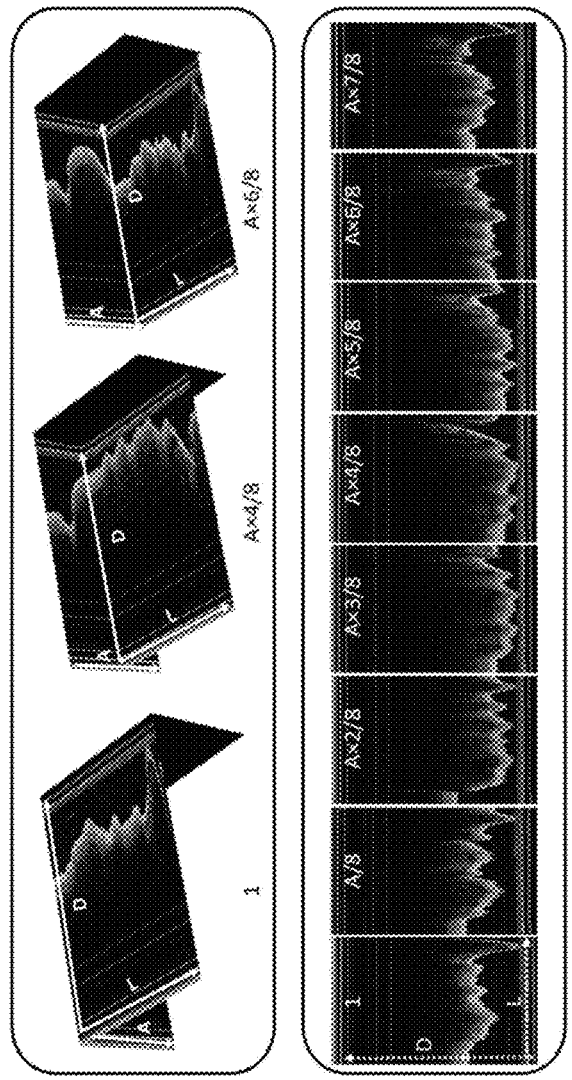
FIG. 9 shows at least one embodiment example of an extraction of a number of A-lines (NA) (e.g., default may be 8 A-lines in one or more embodiments) equally spaced and perpendicular to the catheter or probe cross sections from the 3D A-line volume (see e.g., step S104 in FIG. 3) in accordance with one or more aspects of the present disclosure.
Figure 10:
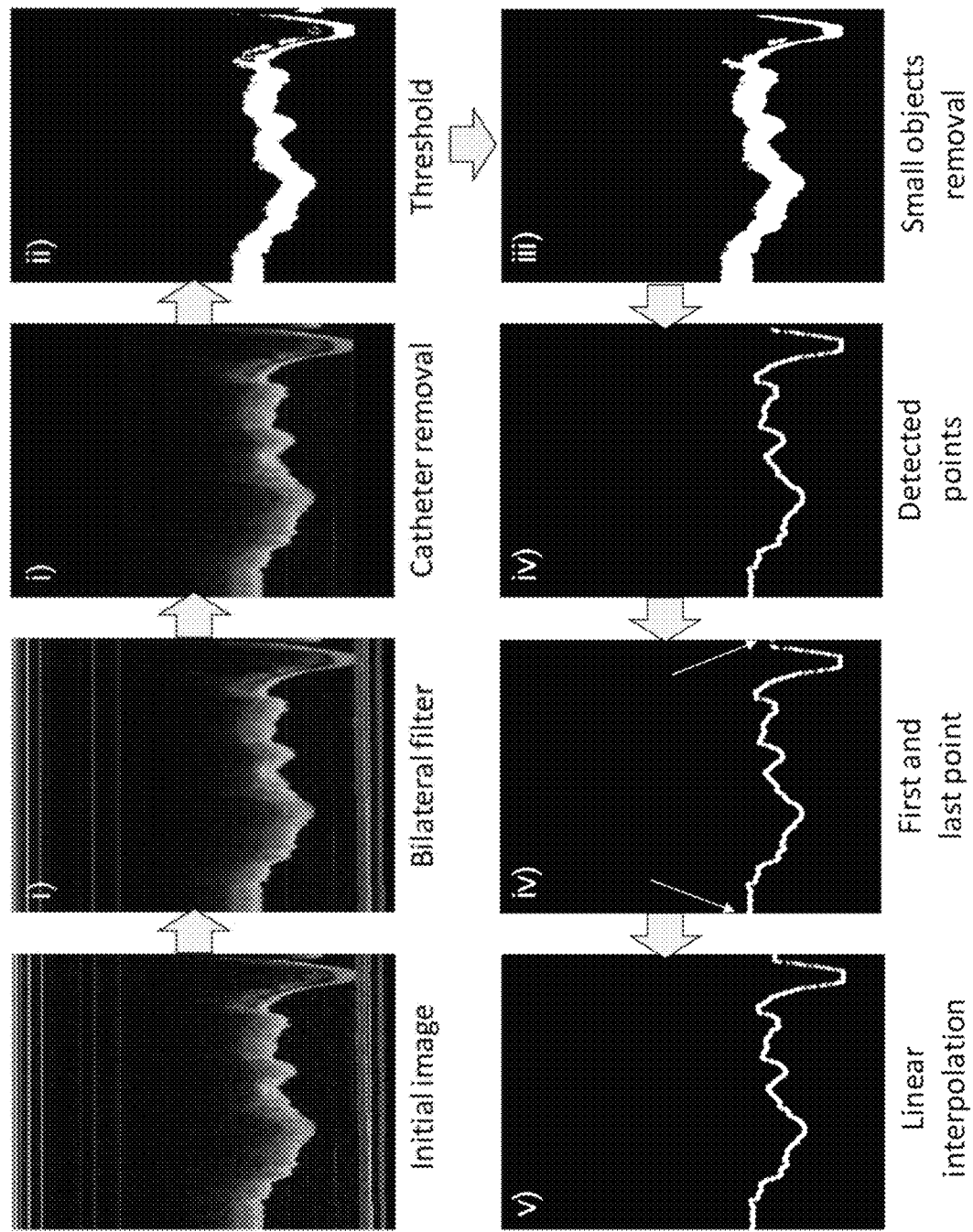
FIG. 10 shows at least one embodiment example of a segmentation procedure of a 3D A-line cross section (see e.g., step S106 in FIG. 3) in accordance with one or more aspects of the present disclosure.

In the subject embodiment example, a fast method to automatically calculate the distance of the catheter or probe (e.g., the catheter or probe 120) to the lumen border (e.g., the lumen border 61 as shown in FIG. 6) for each A-line is described. As discussed above, at least one embodiment example of the overall workflow of one or more A-line distance calculation methods is show in FIG. 3. One or more embodiments of A-line distance calculation method(s) may include the following details. For example, first (e.g., in one or more embodiments of step S102 of FIG. 3), each block of A-lines: A×D, where A is the number of A-lines and D is the A-line depth, corresponds to an OCT image (2D A-lines) and may be stored to a 3D matrix, which forms a 3D A-line volume (for example, as shown in FIG. 8): A×D×L, where L is the number of the pullback frames. Then (e.g., in one or more embodiments of step S104 of FIG. 3), from the 3D A-line volume, NA equally spaced and perpendicular to the catheter cross sections are extracted as shown in FIG. 9. NA represent the angle interval of the OCT image (see portion C of FIG. 4) and by default is set to 45° in one or more embodiments, and one or more embodiments may give the user the choice to increase or decrease the interval. One or more embodiments may set the intervals using the following: the smaller the NA is, the more precise the A-line distance may be.

Thereafter (e.g., in one or more embodiments of step S106 of FIG. 3), the border line of each 3D A-line cross section may be detected using the following method(s): (i) applying bilateral filtering and deleting the catheter (e.g., the catheter or probe 120) (see e.g., images for step (i) in FIG. 10); (ii) applying automatic thresholding, such as, but not limited to, Otsu's automatic thresholding (see example discussion below regarding same; see also, image for step (ii) in FIG. 10); (iii) smoothing the segmented images by deleting objects or small objects which correspond to image artifacts (see e.g., image for step (iii) in FIG. 10); (iv) scanning the image from bottom to top (or another direction, e.g., from top to bottom, side to side, etc.), storing the first non-zero pixel and if the y coordinate of the first $(x_1,y_1)$ and last $(x_{end},y_{end})$ detected point differ from the first $(c_1)$ and last $(c_{end})$ column of the image, respectively, then adding as first point: $(x_1,c_1)$ and as last point: $(x_1,c_{end})$ (see e.g., images for step (iv) in FIG. 10); and finally (v) connecting the detected non-zero pixel using a linear interpolation function (see e.g., image for step (v) in FIG. 10). As discussed above, FIG. 10 presents schematically the segmentation of a 3D A-line cross section in correspondence with the previously described method embodiment steps.

Bilateral Filtering:

Similarly to Gaussian filters, bilateral filters are non-linear smoothing filters. The fundamental difference is that bilateral filters take into account the pixels intensity differences, which result in achieving edge maintenance simultaneously with noise reduction. Using convolutions, a weighted average of the neighborhood pixels' intensities may replace the intensity of the mask's central pixel. In one or more embodiments, the bilateral filter for an image I, and a window mask W is defined as:

$$I'(x) = \frac{1}{W_p}\sum_{x_i \in w} I(x_i) f_r(\|I(x_i) - I(x)\|) g_s(\|x_i - x\|),$$

having a normalization factor $W_p$: $W_p = \sum_{x_i \in w} f_r(\|I(x_i)-I(x)\|) g_s(\|x_i-x\|)$, where x are the coordinates of the mask's central pixel and the parameters $f_r$ and $g_s$ are the Gaussian kernel for smoothing differences in intensities and the spatial Gaussian kernel for smoothing differences in coordinates.

Otsu's Thresholding:

To automatically threshold the 3D A-line cross section images in one or more embodiments, a threshold $Thr_{otsu}$ for the image I' may be calculated using the Otsu's method, and the pixels of the image I' that are smaller than $Thr_{otsu}$ may be set to a zero value. The result is a binary image with the arterial wall represented by the non-zero objects. Since the non-zero objects also may correspond to image artifacts, an extra step may be applied in one or more embodiments: detecting the objects that are smaller than a predetermined area, such as, but not limited to, a whole catheter or probe area, 3% of the whole image, etc. Using this extra step, we ensure that only the objects that correspond to the wall area will be used to detect the border.

Figure 11:
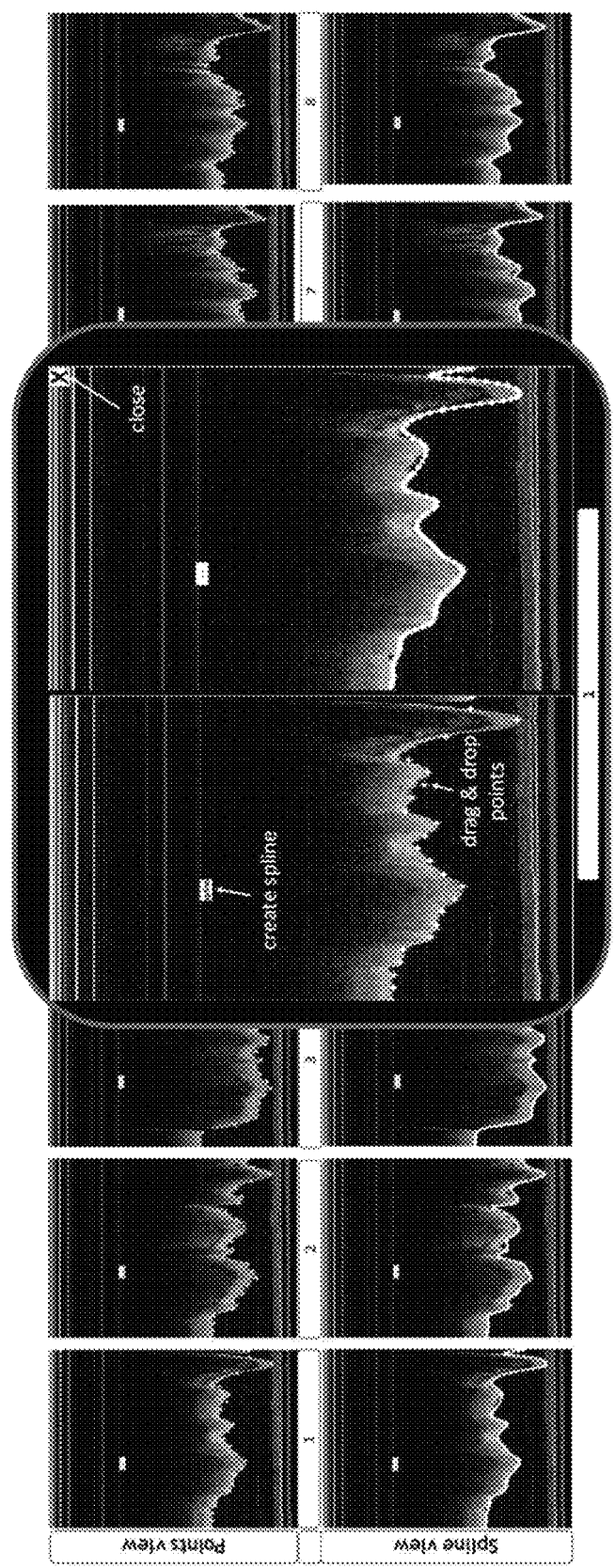
FIG. 11 shows at least one embodiment of a representative example of a global correction of a cross sectional A-line border detection (see e.g., step S110 in FIG. 3) in accordance with one or more aspects of the present disclosure.

As in any automatic system or algorithm/method, errors may exist or occur. In the present algorithm or method embodiment example, an error may be created in the border detection step. This error may be acceptable by some medical experts and not by other medical experts. In this embodiment, to ensure that the result of the proposed method will be accepted by the majority of medical experts, one or more embodiment examples of methods of the present disclosure give the user the ability to correct the detected A-line borders. This correction may be performed globally, and a representative example is shown in FIG. 11. The number of the detected A-line points may be reduced to 5%, and a B-spline interpolation may be applied to the other 95% of the points in one or more embodiments (in one or more embodiments, the percentages may be modified by a few % (e.g., 3% and 97%, 2% and 98%, 4% and 96%, 6% and 94%, 7% and 93%, 8% and 92%, or any other set, selected, or predetermined split desired by a medical expert or user of the method(s), etc.). Two different views may be shown to the user: the reduced points view and the spline view (see e.g., FIG. 11). The user may visually observe any border inaccuracies in the spline view and then select the corresponding points view, which may open on or in a separate window allowing the user to drag and drop any point. When the user moves the point or points to the desired place, he or she may click the create spline button, and the new spline may be shown in the spline view. Using the spline function, all the points before and after the point, which is moved by the user, change and move according to the new points coordinates. The B-spline (basis spline) method interpolation that is used in the subject embodiment example is a polynomial function crossing some specific points (control points) and has the minimal support with respect to a given smoothness. The curve is defined as a linear combination of control points. For $\lambda+1$ control points: $\{V\}_0^\lambda = \{V_0, V_1, \ldots, V_\lambda\}$, the B-spline defines a $\kappa+1$ number of points between the control points, called knots: $\{U\}_0^\kappa = \{U_0, U_1, \ldots, U_\kappa\}$ as: $\kappa = \lambda+\rho+1$, and a parametric curve as: $b(U) = \sum_{\alpha=1}^\lambda N_{\alpha,\rho}(U) V_\alpha$, where $\rho$ is the spline degree and $N_{\alpha,\rho}$, basic B-spline function. In one or more other embodiments, other interpolation methods may be used.

Later (e.g., in one or more embodiments of step S108 of FIG. 3), the segmented 3D A-line cross sections may be translated to luminal A-line points. This translation may be based on the following specifics: (a) each 3D A-line cross sections image corresponds to a specific point of the 2D A-line frames (see e.g., FIG. 9, and parts A, B, and C of FIG. 12); (b) each column of a 3D A-line cross section image corresponds to one of the L number of frames: column 1-frame 1, column 2-frame 2, . . . column L-frame L; and (c) each point of the detected border line in each 3D A-line cross section (see e.g., step S106 in FIG. 3) corresponds to a specific point within the depth D of each 2D A-line frame (see e.g., FIG. 8 and FIG. 1). At least one embodiment example of the translation of the detected border lines to 2D A-line point(s) is described by the following pseudocode and shown schematically in parts A, B, and C of FIG. 12:

```
for A=1:9
    ImA=cross section(A)
    for l=1:L
        ImB=2D A-line(l)
        for d=1:D
            point=ImA(l,d);
            if point==1
                ImB(d,A)==1;
            end
        end
    end
end
```

In one or more embodiments, following the previous procedure, for each 2D A-line frame, NA lumen points (default NA=8) may be detected which correspond to NA columns of the image: 1, A/(NA−1), A×2/(NA−1), A×3/(NA−1), A×4/(NA−1), A×5/(NA−1), A×6/(NA−1), and A×7/(NA−1). To be able to detect the remaining lumen points, a linear interpolation may be performed. For a pair of points $(x_a, y_a)$, $(x_b, y_b)$, their linearly interpolated point (x,y) of a known x may be calculated as:

$$y = y_a + (y_b - y_a)\frac{x - x_a}{x_b - x_a}$$

Figure 12:
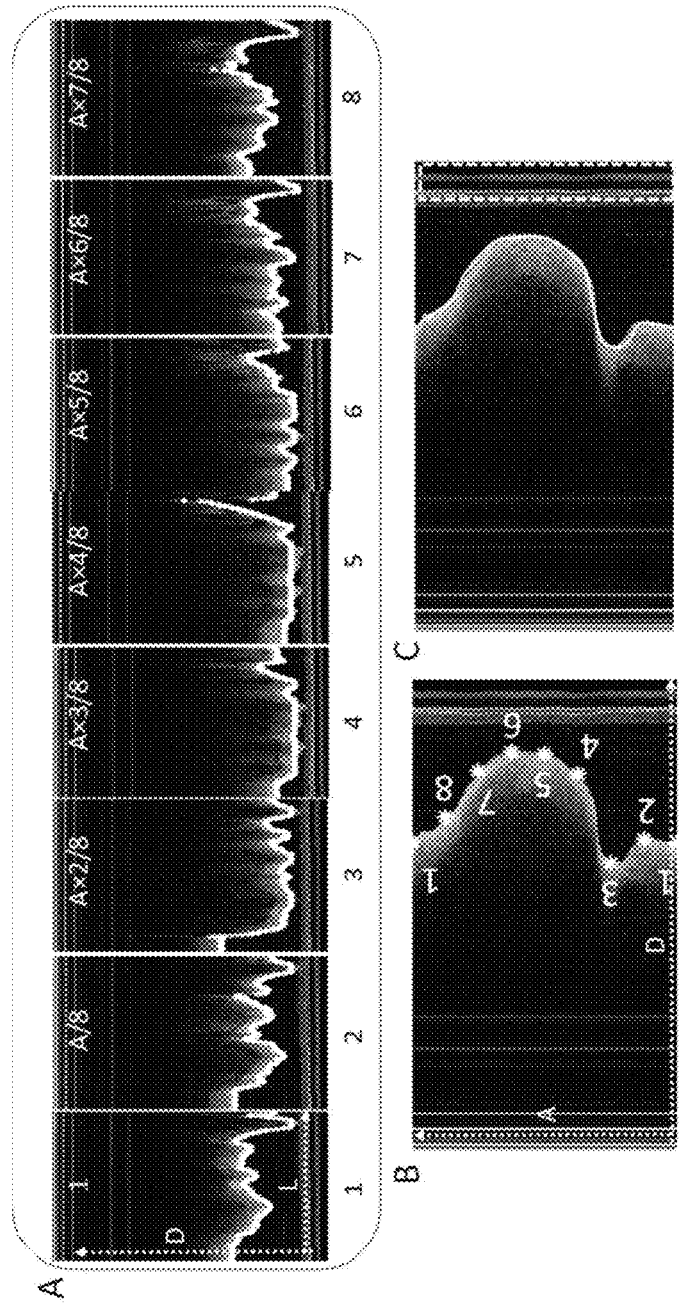
FIG. 12 shows at least one embodiment example of a segmentation of the 8 (default NA in one or more embodiments; default may be another predetermined or set number in one or more embodiments) 3D A-line cross-sections (e.g., part A may correspond to S106, part B and part C may correspond to S108, etc.) in accordance with one or more aspects of the present disclosure.
Figure 13:
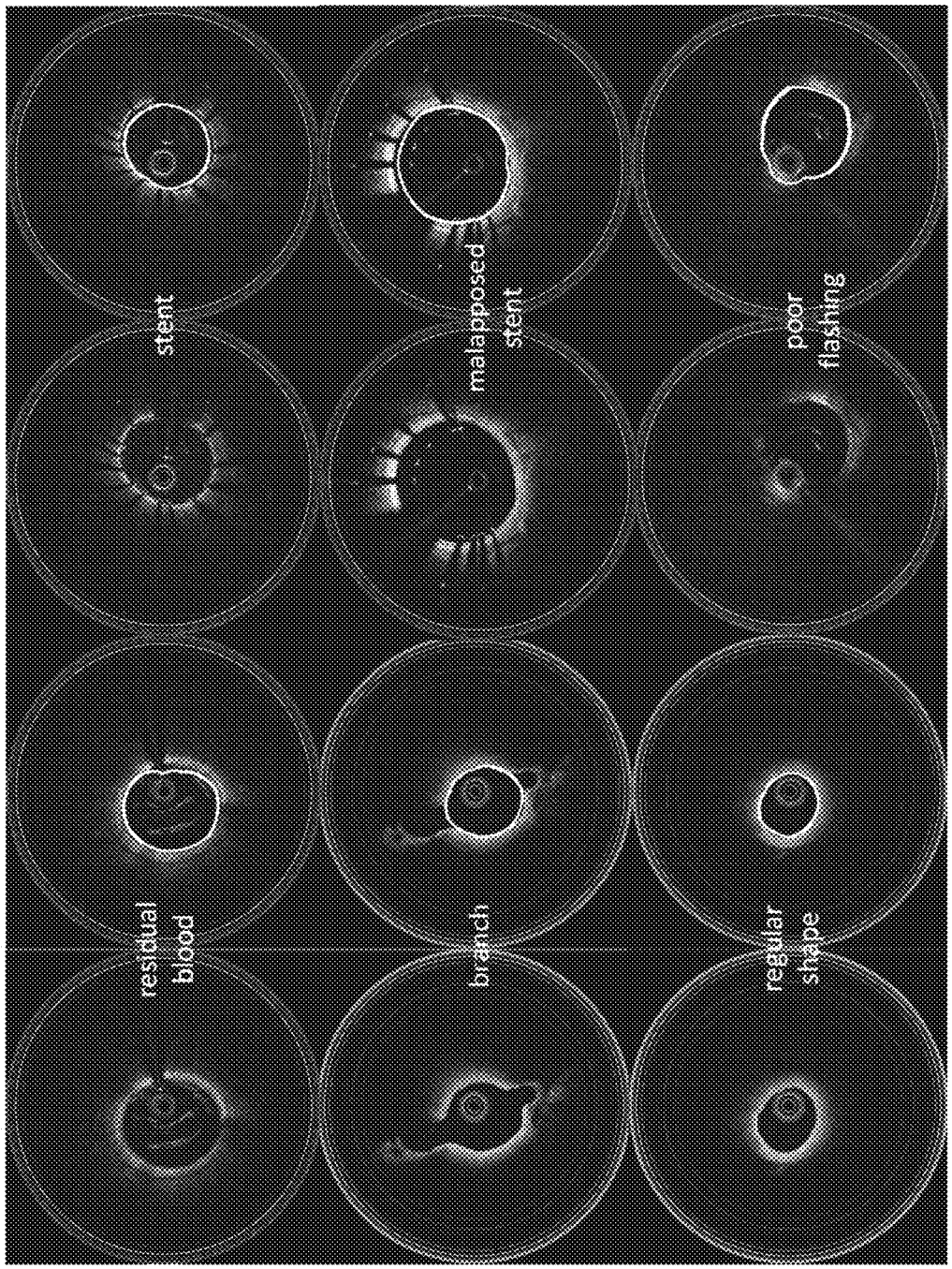
FIG. 13 shows examples of the lumen transformation from A-lines to Cartesian coordinates superimposed over their corresponding OCT images having: residual blood, side branches, regular shaped vessel, stented and poor flashing areas (see e.g., S114) in accordance with one or more aspects of the present disclosure.

(see e.g., part C of FIG. 12). Later (in one or more embodiments of step S112 of FIG. 3), a method may further include, for each A-line, measuring the number of pixels from the lumen border to the catheter border (known distance), and multiplying them to the pixel spacing distance in order to estimate the distance.

Figure 14:
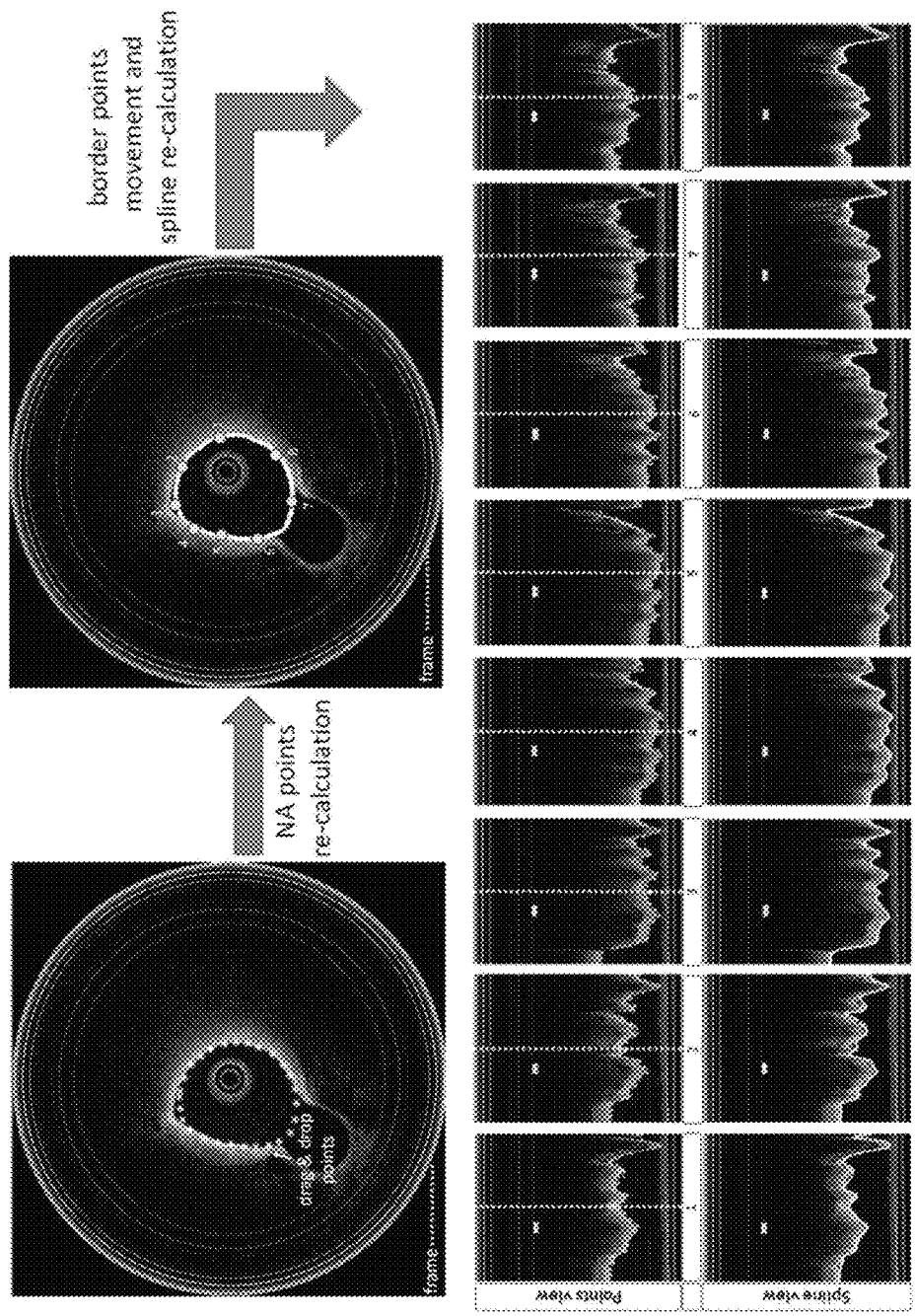
FIG. 14 shows at least one embodiment example of a global correction of an OCT lumen border (see e.g., S110) in accordance with one or more aspects of the present disclosure.
Figure 15:
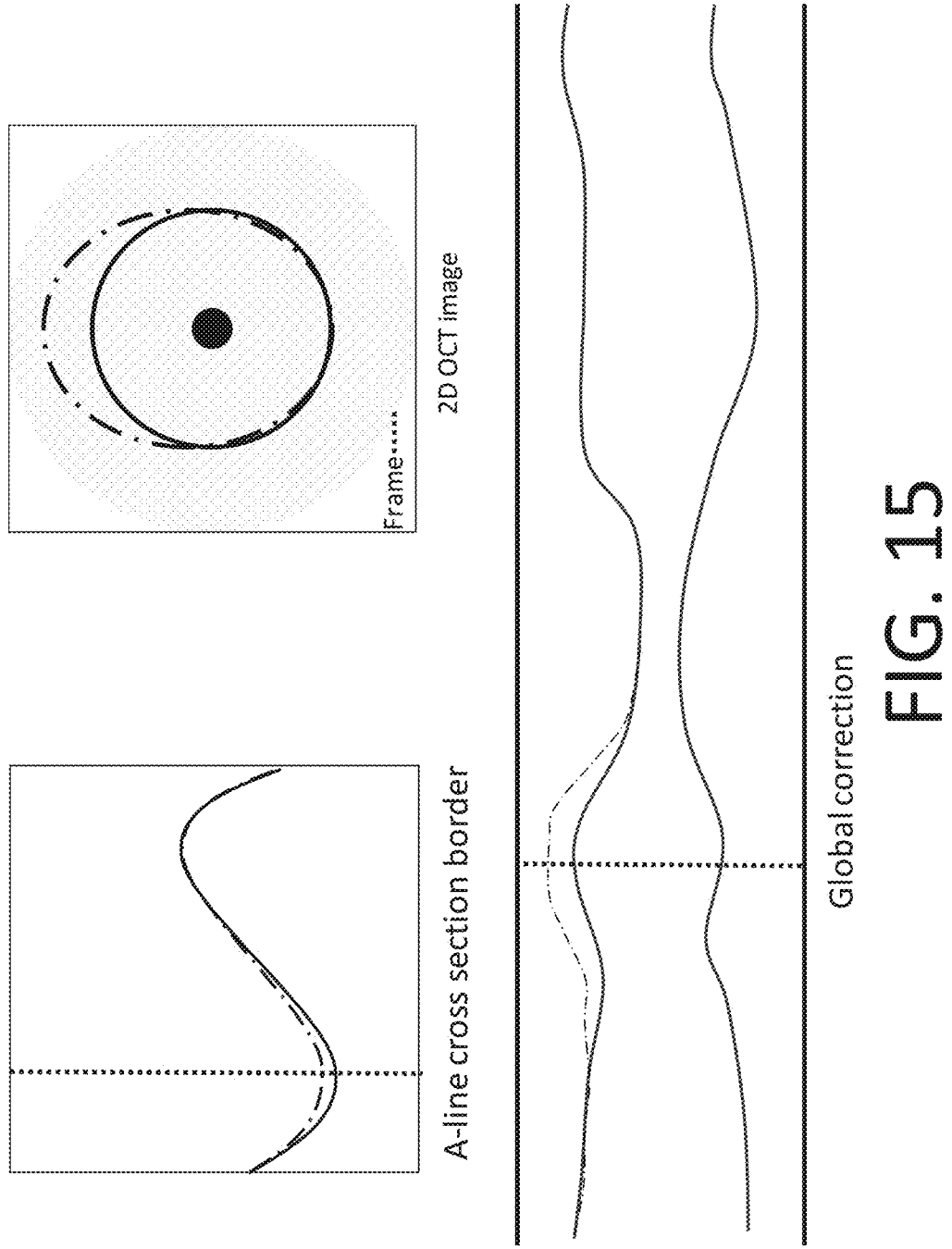
FIG. 15 shows at least embodiment example of a schematic description of a global correction happening on an A-line cross section border or on an OCT lumen border (see e.g., S110) in accordance with one or more aspects of the present disclosure.

Finally (in one or more embodiments of step S114 in FIG. 3), each of the detected lumen 2D A-line points and the 2D A-line images may be translated to Cartesian coordinates: $(r,\theta) \rightarrow i,j$, where r represents the range dimension, $\theta$ the acquisition angle, $i = r \cos \theta$ and $j = r \sin \theta$ (see e.g., FIG. 13). Following the same rationale as for the detected borders of A-line cross sections (see e.g., step S106 of FIG. 3), one or more embodiments of the method(s) may allow for another global correction (see e.g., step S110 of FIG. 3) if the user desires. In the current global correction example, the user may drag and drop the OCT lumen border, and then automatically the NA points may be recalculated and may move the spline of the 2D A-line cross sections, correcting globally the lumen borders in all the OCT frames (see e.g., FIG. 14). A schematic description of the global correction happening on the A-line cross section border or on the OCT lumen border is shown in FIG. 14.

Figure 16B:
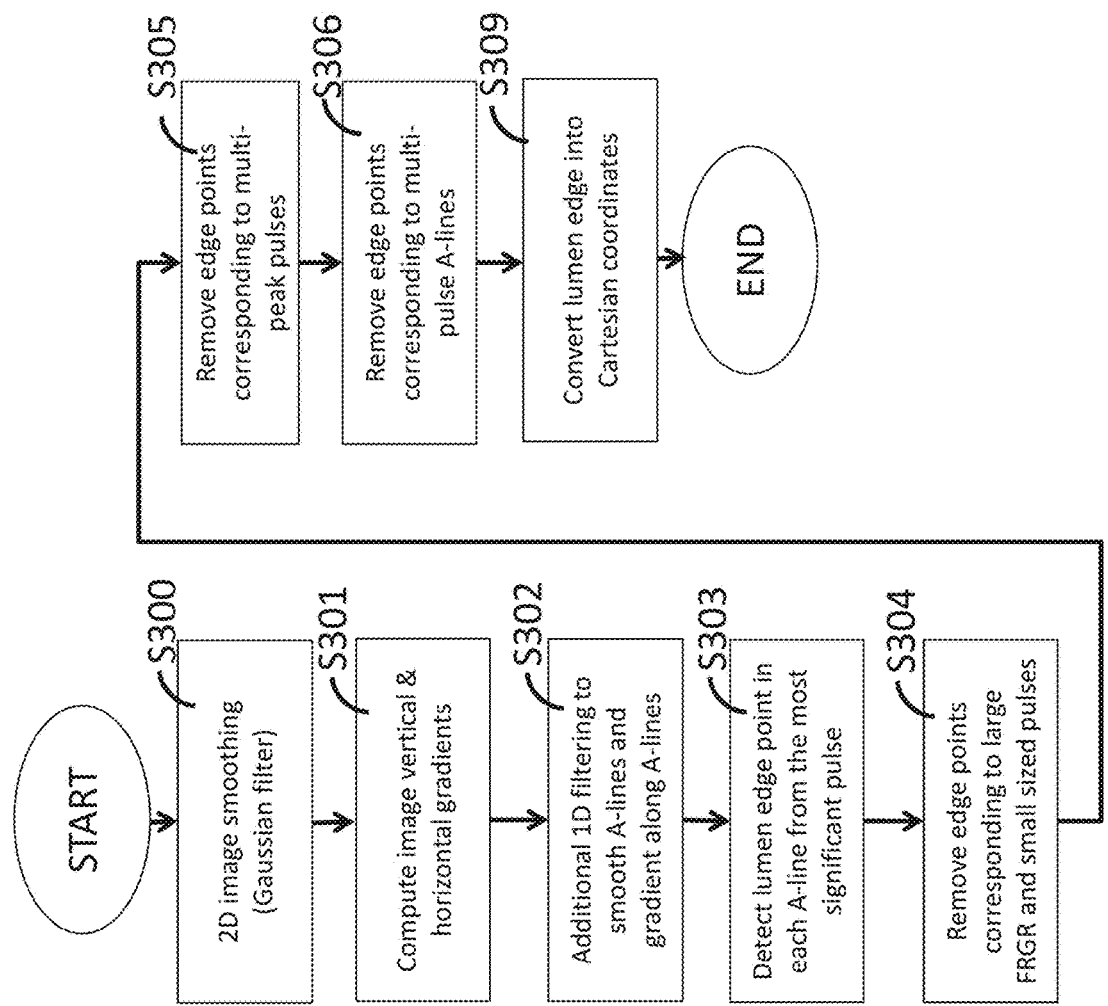

In accordance with at least one aspect of the present disclosure and as aforementioned, one or more additional methods for lumen, stent, and/or artifacts detection of OCT images, processing of intravascular image data, and/or calculating A-line lumen distances are provided herein, or may be used with one or more of the features or aspects of the present disclosure, and are discussed in U.S. patent application Ser. No. 16/414,222, filed on May 16, 2019, the entire disclosure of which is incorporated by reference herein in its entirety, and are discussed in U.S. Pat. App. No. 62/944,064, filed on Dec. 5, 2019, the entire disclosure of which is incorporated by reference herein in its entirety. For example, FIG. 16A illustrates a flow chart of at least one embodiment of a method for lumen, stent, and/or artifacts detection of OCT image(s) that may be used with one or more methods for processing of intravascular image data and/or calculating A-line lumen distances as discussed herein. Preferably, the method(s) may include one or more of the following: (i) performing two dimensional (2D) image smoothing (e.g., using a lowpass filter, using a Gaussian filter, etc.) (see step S300 of FIG. 16A); (ii) computing image vertical and horizontal gradients (see step S301 of FIG. 16A); (iii) smoothing A-lines and gradient along A-lines (e.g., using one dimensional (1D) filtering) (see step S302 of FIG. 16A); (iv) detecting a lumen edge point(s) in each A-line from the most significant pulse (e.g., the most significant pulse may be the pulse with the highest amplitude or the pulse with the largest underlying area determined by applying a size criterion or size criteria (e.g., width criterion, area under the pulse criterion, etc.) where different size criteria may produce similar results) (see step S303 of FIG. 16A); (v) removing edge points corresponding to a large falling and rising gradient ratio (FRGR) (e.g., the most significant pulse in the A-line that has a steep falling edge comparable to the rising edge, that produces a larger FRGR value, etc.) and small sized pulses (e.g., the most significant pulse in the A-line with the pulse amplitude or the area underlying the pulse below a threshold, etc.) (see step S304 of FIG. 16A); (vi) removing edge point(s) corresponding to multi-peak pulse(s) (see step S305 of FIG. 16A); (vii) removing edge point(s) corresponding to multi-pulse A-line(s) (see step S306 of FIG. 16A); (viii) filling the gaps in the lumen edge using interpolation (e.g., via median filtering the lumen edge) to form the lumen edge (e.g., forming the lumen edge from the most significant pulse locations of all the A-lines) (see step S307 of FIG. 16A); (ix) filtering or smoothing the lumen edge (e.g., using low pass filtering, such as 1D lowpass filtering and/or median filtering, etc.) (see step S308 of FIG. 16A); and (x) converting the lumen edge into Cartesian coordinates (see step S309 of FIG. 16A). One or more embodiments of a method(s) for detecting lumen and artifacts may be performed with or without the filtering of the lumen edge (e.g., step S307 and/or step S308 of FIG. 16A may be removed as shown in FIG. 16B). For example, median filtering and/or low pass filtering the lumen edge is optional in one or more embodiments. In one or more embodiments, alternative methods for smoothing the lumen edge may be used in place of the median filtering and/or low pass filtering of the lumen edge.

A computer, such as the console or computer 1200, 1200', may perform any of the steps, processes, and/or techniques discussed herein for any apparatus and/or system being manufactured or used, including, but not limited to, apparatus or system 100, apparatus or system 100', apparatus or system 100'', apparatus or system 100''', any of the embodiments shown in FIGS. 3-22, any other apparatus or system discussed herein, etc.

Figure 17:
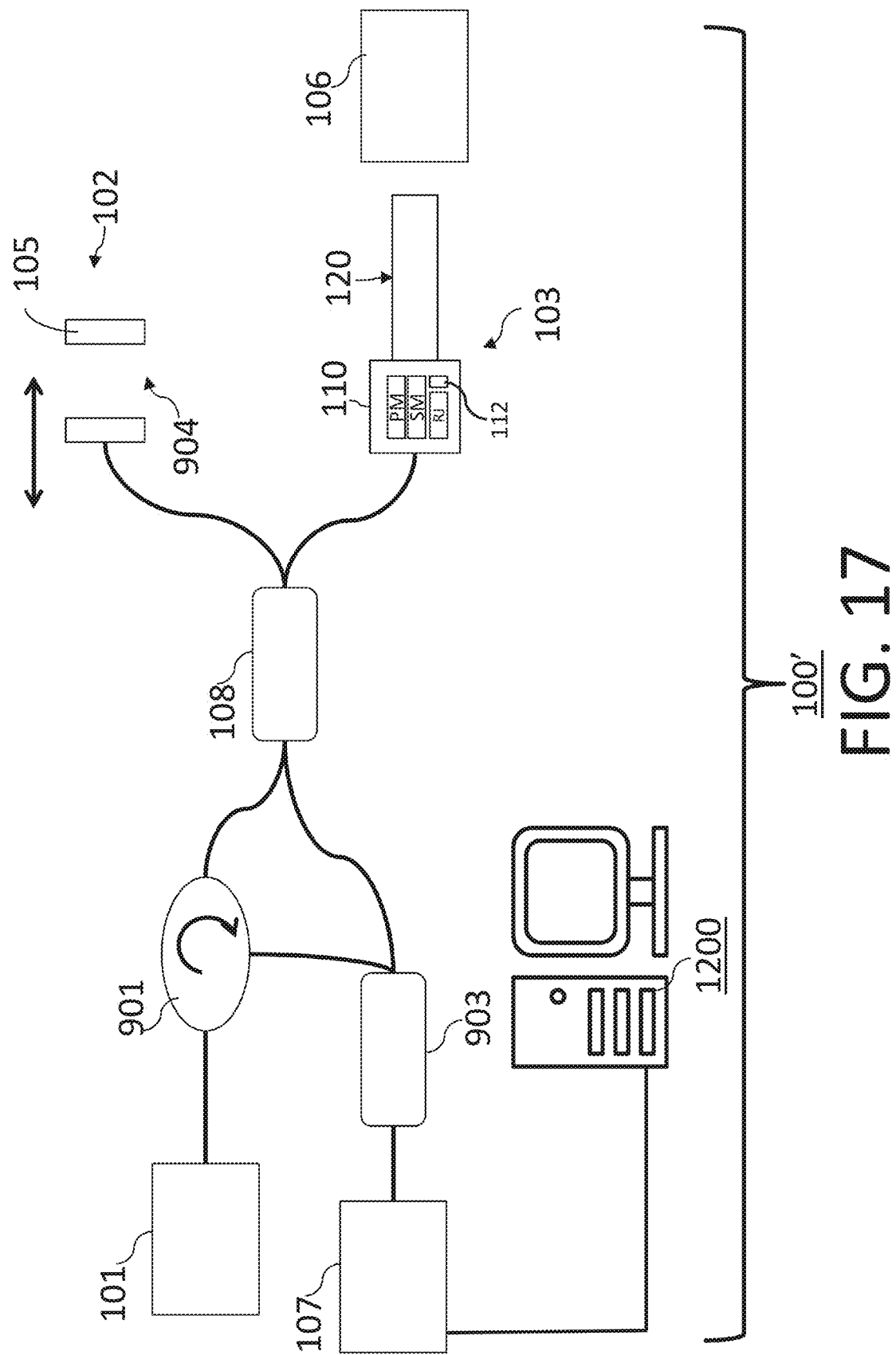
FIG. 17 shows at least one embodiment of an OCT apparatus or system for utilizing one or more embodiments of real-time lumen distance calculation methods and/or techniques in accordance with one or more aspects of the present disclosure.

In accordance with one or more further aspects of the present disclosure, bench top systems may be utilized with the techniques, such as, but not limited to, the real time lumen distance calculation techniques, disclosed herein. FIG. 17 shows an example of a system that can utilize the lumen distance calculation techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target, patient (e.g., a blood vessel of a patient), an object 106, etc. in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 17-19 and 21 discussed further below), the computer

1200' (see e.g., FIG. 22 discussed further below), etc. Additionally or alternatively, one or more of the computers, CPUs, processors, etc. discussed herein may be used to process, control, update, emphasize, and/or change one or more of the multiple imaging modalities, and/or process the related techniques, functions or methods (e.g., the lumen distance calculation(s)), or may process the electrical signals as discussed above.

Figure 18:
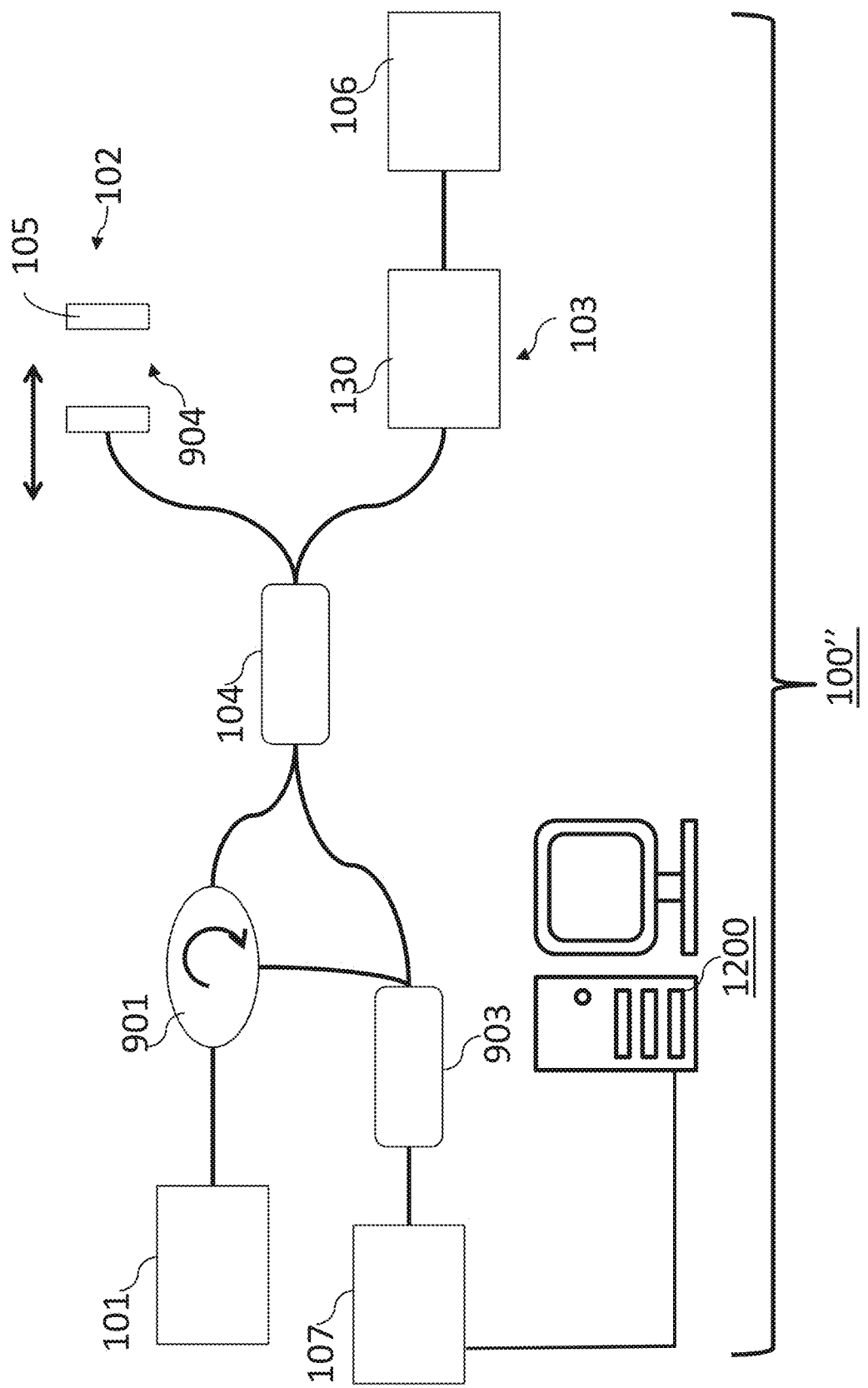
FIG. 18 shows at least another embodiment of an OCT apparatus or system for utilizing one or more embodiments of real-time lumen distance calculation methods and/or techniques in accordance with one or more aspects of the present disclosure.

In one or more embodiments, the sample arm 103 may include a phase shift unit 130 for a bench top system(s) as shown in system 100" in FIG. 18. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 17-19) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, lumen distance, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 19:
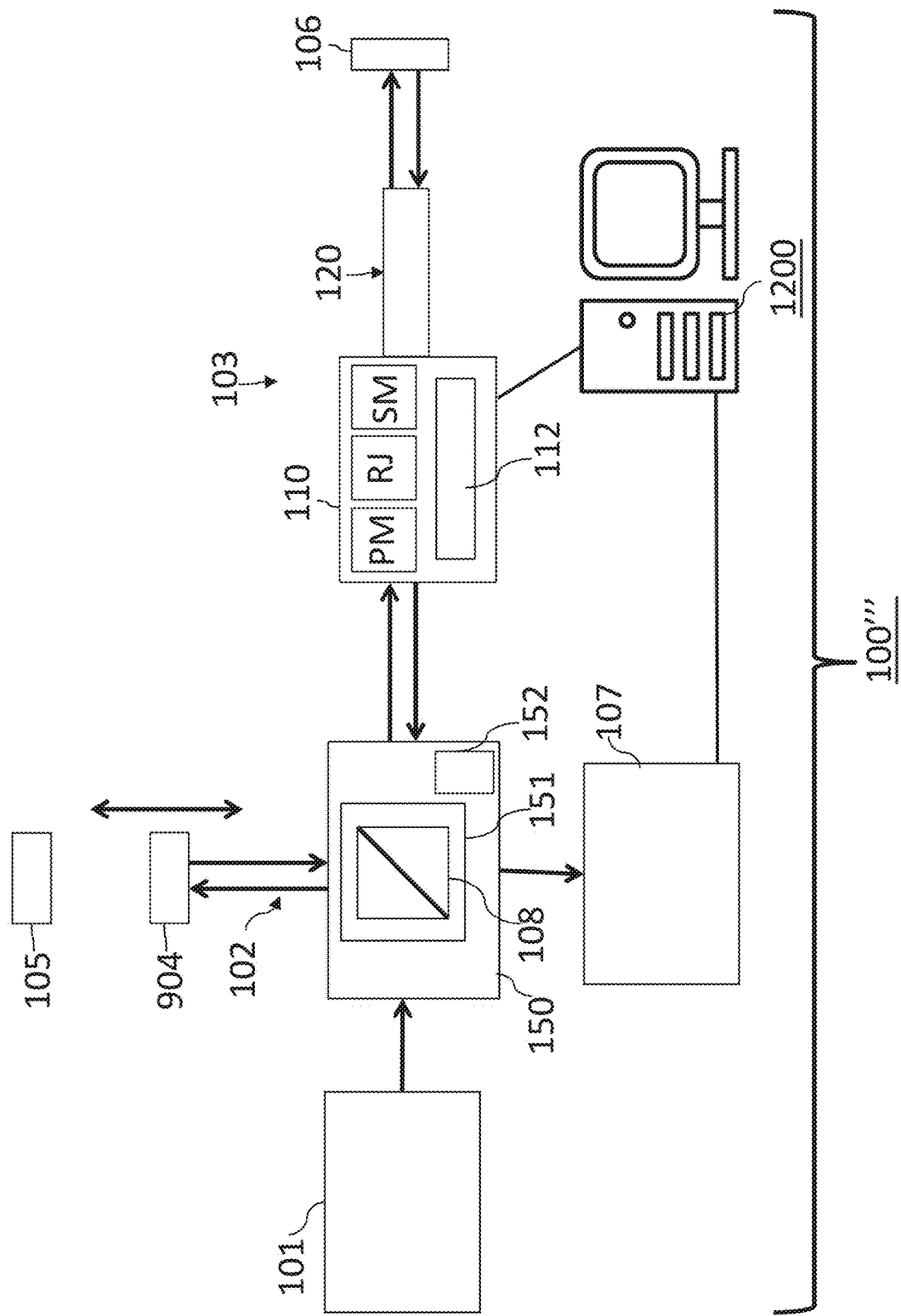
FIG. 19 shows at least a further embodiment of an OCT apparatus or system for utilizing one or more embodiments of real-time lumen distance calculation methods and/or techniques in accordance with one or more aspects of the present disclosure.

In accordance with one or more further aspects of the present disclosure, one or more other systems may be utilized with the lumen distance calculation techniques disclosed herein. FIG. 19 shows an example of a system 100''' that may utilize the detecting and guiding techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 17-19 and 21 discussed further below), the computer 1200' (see e.g., FIG. 22 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIGS. 17 and 19). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Preferably, in one or more embodiments including the deflecting or deflected section 108 (best seen in FIGS. 17-19), the deflected section 108 operates to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", 100''', any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc. One or more features of the aforementioned configurations of at least FIGS. 1-22 may be incorporated into one or more of the systems, including, but not limited to, the system 100, 100', 100", 100''', discussed herein.

While not limited to such arrangements, configurations, devices or systems, one or more embodiments of the devices, apparatuses, systems, methods, storage mediums, GUI's, etc. discussed herein may be used with an apparatus or system as aforementioned, such as, but not limited to, for example, the system 100, the system 100', the system 100", the system 100''', the devices, apparatuses, or systems of FIGS. 1-22, any other device, apparatus or system discussed herein, etc. In one or more embodiments, one user may perform the method(s) discussed herein. In one or more embodiments, one or more users may perform the method(s) discussed herein. In one or more embodiments, one or more of the computers, CPUs, processors, etc. discussed herein may be used to process, control, update, emphasize, and/or change one or more of the multiple imaging modalities, to calculate lumen distance(s), and/or process the related techniques, functions or methods, or may process the electrical signals as discussed above.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, performing control, viewing, changing, emphasizing methods for one or more imaging modalities and/or any other method discussed herein. The light source 101 may be fiber coupled or may be free space coupled to the other components of the apparatus and/or system 100, 100', 100'', 100''', the devices, apparatuses or systems of FIGS. 1-22, or any other embodiment discussed herein. As aforementioned, the light source 101 may be a swept-source (SS) light source.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC). The one or more detectors may be detectors having structure as shown in one or more of FIGS. 1-22 and as discussed above.

The one or more detectors 107 may transmit the digital or analog signals to a processor or a computer such as, but not limited to, an image processor, a processor or computer 1200, 1200' (see e.g., FIGS. 1, 17-19, and 21-22), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS. 1-22, the computer 1200, the computer 1200', the image processor, may also include one or more components further discussed herein below (see e.g., FIGS. 21-22).

In at least one embodiment, a console or computer 1200, 1200' operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 17-19 and FIG. 21 and/or the console 1200' of FIG. 22 as further discussed below). In one or more embodiments, the MCU 112 or the motor M operates to change a speed of a motor of the RJ and/or of the RJ. The motor may be a stepping or a DC servo motor to control the speed and increase position accuracy (e.g., compared to when not using a motor, compared to when not using an automated or controlled speed and/or position change device, compared to a manual control, etc.).

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100'', 100''', and/or the detector(s) 107 thereof, and/or from the devices, apparatuses, or systems of FIGS. 1-22, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems/apparatuses, such as, but not limited to, the system 100, the system 100', the system 100'', the system 100''', the systems/apparatuses of FIGS. 3-22, etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100'', the system 100''', etc. as discussed herein. Those skilled in the art will appreciate that alternative embodiments of the system 100, the system 100', the system 100'', the system 100''', the systems/apparatuses of FIGS. 3-22, and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100'' and the system 100''', the systems/apparatuses of FIGS. 3-22, any other embodiment, etc. as discussed herein, there are similarities between the apparatuses/systems discussed herein. Likewise, while the console or computer 1200 may be used in one or more systems (e.g., the system 100, the system 100', the system 100'', the system 100''', the systems/apparatuses of FIGS. 3-22, etc.), one or more other consoles or computers, such as the console or computer 1200', may be used additionally or alternatively.

Figure 20:
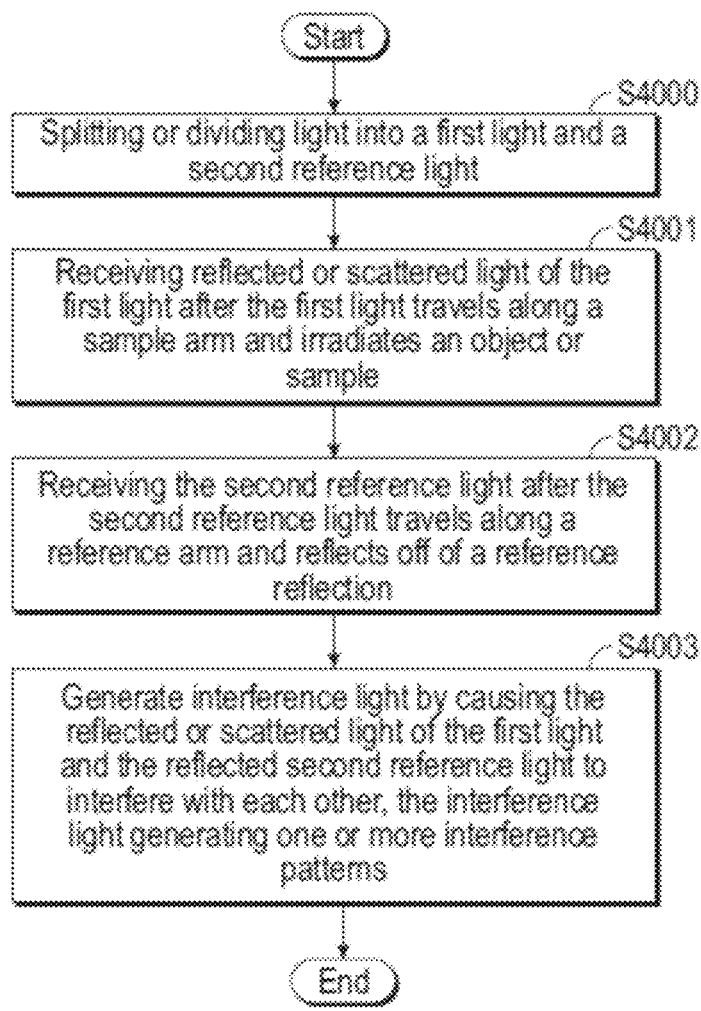
FIG. 20 is a flow diagram showing a method of performing an imaging feature, function or technique in accordance with one or more aspects of the present disclosure.

In accordance with one or more aspects of the present disclosure, one or more methods for detecting and guiding optical connections are provided herein, and one or more methods for performing imaging are provided herein. FIG. 20 illustrates a flow chart of at least one embodiment of a method for performing imaging. Preferably, the method(s) may include one or more of the following: (i) splitting or dividing light into a first light and a second reference light (see step S4000 in FIG. 20); (ii) receiving reflected or scattered light of the first light after the first light travels along a sample arm and irradiates an object or a sample (see step S4001 in FIG. 20); (iii) receiving the second reference light after the second reference light travels along a reference arm and reflects off of a reference reflection (see step S4002 in FIG. 20); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 20). One or more methods may further include using low frequency monitors to update or control high frequency content to improve image quality. For example, one or more embodiments may use balanced detection, polarization diversity, automated polarization control, calculated lumen distance(s), etc. to achieve improved image quality. In one or more embodiments, an imaging probe may be connected to one or more systems (e.g., the system 100, the system 100', the system 100", the system 100''', the devices, apparatuses or systems of FIGS. 3-22, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

There are many ways to compute power and/or detect lumen edge(s) and artifact(s), and/or calculate lumen distance(s), digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1, 17-19, and 21), a computer 1200' (see e.g., FIG. 22), etc. as discussed further below, via cable(s) or wire(s), such as, but not limited to, the cable(s) or wire(s) 113 (see FIG. 21). Additionally or alternatively, the computers or processors discussed herein are interchangeable, and may operate to perform any of the feature(s) and method(s) discussed herein.

Figure 21:
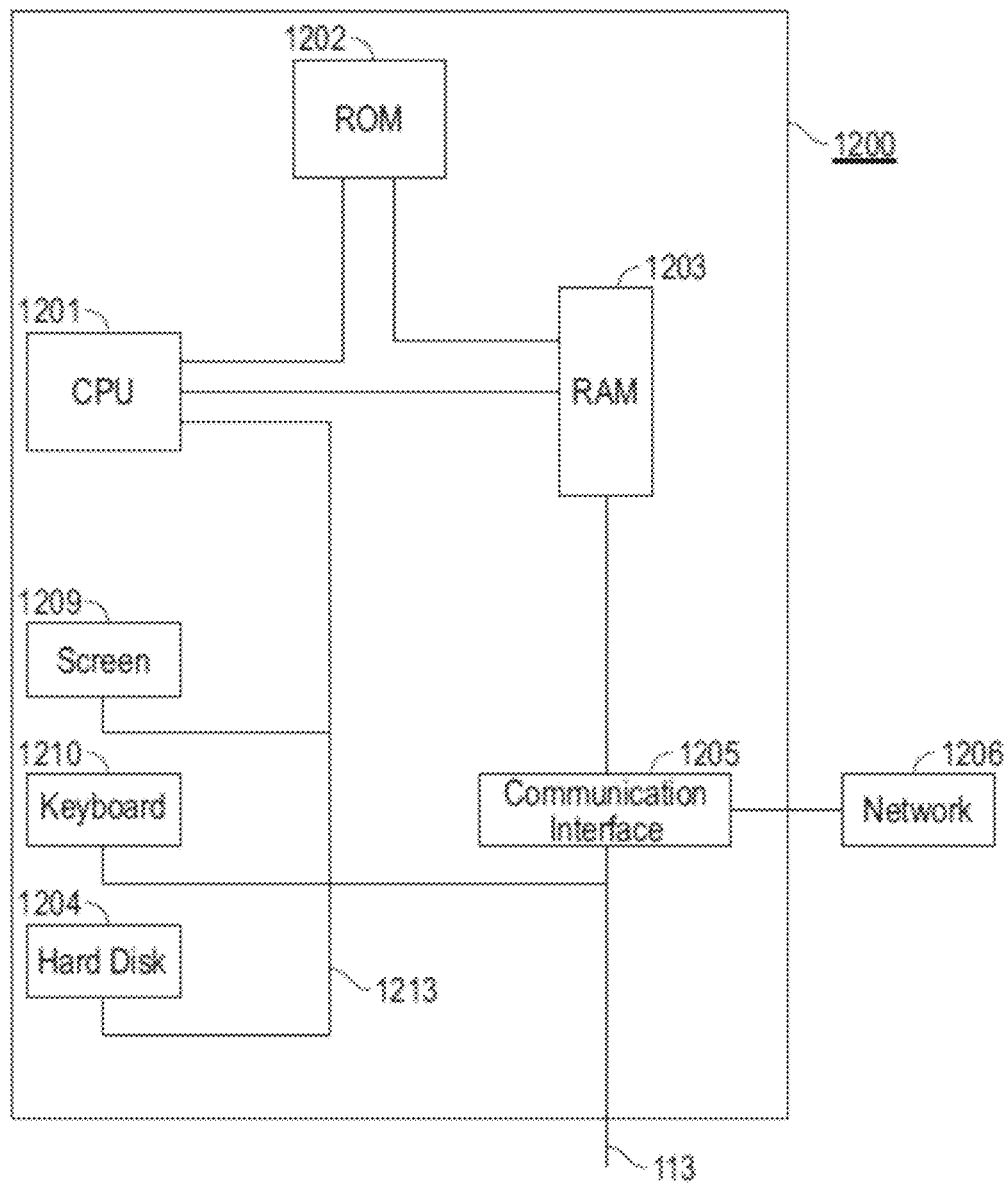
FIG. 21 shows a schematic diagram of an embodiment of a computer that may be used with one or more embodiments of an apparatus or system or one or more methods discussed herein in accordance with one or more aspects of the present disclosure.

Various components of a computer system 1200 (see e.g., the console or computer 1200 as shown in FIGS. 1 and 17-19) are provided in FIG. 21. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS (or "Bus") or other connection lines (e.g., connection line 1213) between one or more of the aforementioned components (e.g., as shown in FIG. 21). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100", the system 100''', and/or the systems/apparatuses of FIGS. 3-22, discussed herein above, via one or more lines 1213), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, artifact(s) detection, and/or lumen distance calculation technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling, calculation, and/or using technique(s) may be controlled remotely).

Figure 22:
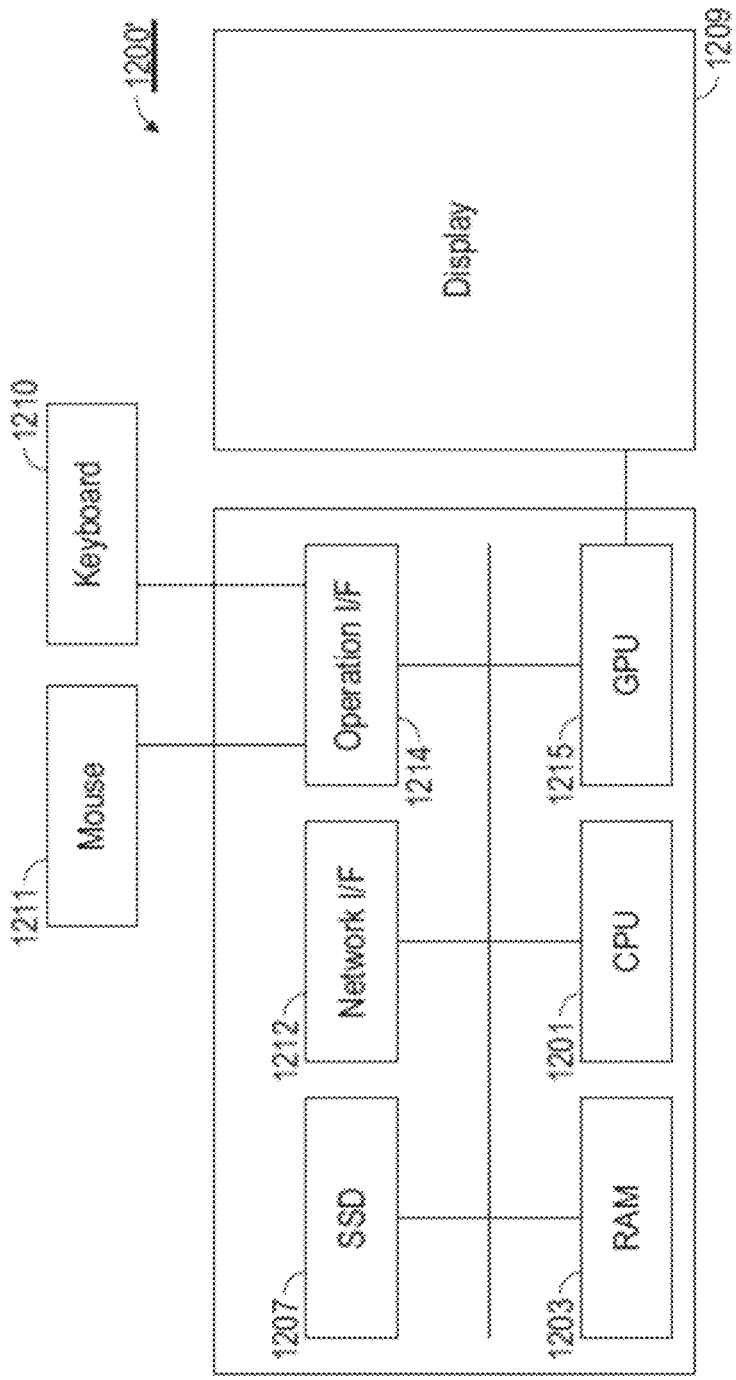
FIG. 22 shows a schematic diagram of another embodiment of a computer that may be used with one or more embodiments of an imaging apparatus or system or methods discussed herein in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 22), a touch screen or screen 1209, a light pen and so on. The communication interface of the computer 1200 may connect to other components discussed herein via line 113 (as diagrammatically shown in FIG. 21). The Monitor interface or screen 1209 provides communication interfaces thereto.

Any methods and/or data of the present disclosure, such as, but not limited to, the methods for using and/or manufacturing a device, system or storage medium for use with same and/or method(s) for imaging, performing tissue or sample characterization or analysis, performing diagnosis, planning and/or examination, detecting lumen edge(s), stent(s), and/or artifact(s), including in OCT image(s), and/or for calculating lumen distance(s), as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 22), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined, limited, or short period(s) of time and/or only in the presence of power, such as, but not limited to Random Access Memory (RAM), register memory, processor cache (s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 21. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 21 or FIG. 22) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 2, 1200, 1200', etc.) may include the aforementioned CPU structure, or may be connected to such CPU structure for communication therewith.

As aforementioned, hardware structure of an alternative embodiment of a computer or console 1200' is shown in FIG. 22. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 17, RJ of FIG. 19, etc.), the motor PM, the motor SM, and/or one or more other components of a system (e.g., the system 100, the system 100', the system 100", the system 100''', the systems/apparatuses of FIGS. 3-22, etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

At least one computer program is stored in the SSD 1207, and the CPU 1201 loads the at least one program onto the RAM 1203, and executes the instructions in the at least one program to perform one or more processes described herein, as well as the basic input, output, calculation, memory writing, and memory reading processes.

The computer, such as the computer 1200, 1200', communicates with the PIU 110, the rotary junction (e.g., the RJ, etc.), the motor PM, the motor SM, the MCU 112, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of lumen edge(s) and/or artifact(s), and/or calculating lumen distance(s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', the systems/apparatuses of FIGS. 3-22, etc.) to set or change the imaging condition, and to start or end the imaging, and/or to start or end the lumen detection, stent(s) detection, artifact(s) detection, and/or calculation of lumen distance(s). The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes.

Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, 2016/0228097, 2018/0045501, and 2018/0003481, each of which patents, patent publications and patent application(s) are incorporated by reference herein in their entireties. As aforementioned, any feature or aspect of the present disclosure may be used with the features disclosed in WO 2016/144878, which is incorporated by reference herein in its entirety. As aforementioned, any feature or aspect of the present disclosure may be used with OCT imaging systems, apparatuses, methods, storage mediums or other aspects or features as discussed in U.S. Pat. Pub. 2019/0298174; U.S. patent application Ser. No. 16/131,662; U.S. patent application Ser. No. 16/414,222, filed on May 16, 2019; U.S. Pat. App. No. 62/901,472; U.S. Pat. App. No. 62/925,655; and U.S. Pat. App. No. 62/944,064, filed on Dec. 5, 2019, each of which patent(s), publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications, equivalent structures, and functions.

The invention claimed is:

1. An imaging device comprising:
one or more processors that operate to:
detect a vessel lumen border or borders using an intravascular imaging signal;
calculate distance from the lumen border or borders to a catheter or probe based on one or more three-dimensional A-line signals;
depict the lumen border or borders in each two-dimensional (2D) Optical Coherence Tomography (OCT) frame allowing for a global correction;
allow detection of the vessel lumen borders in all data for a pullback; and
allow for a more detailed detection in a case where an angle interval (AN) is specified that is smaller or larger than a default angle interval.

2. The imaging device of claim 1, wherein one or more of the following:
(i) the pullback data includes data having noise, and one or more branch areas for a vessel; and
(ii) a user of the imaging device specifies the smaller or larger angle interval.

3. The imaging device of claim 1, wherein the one or more processors further operate to:
obtain or receive two-dimensional (2D) A-lines;
construct a 3D A-line volume matrix from the 2D A-lines, where the 3D A-line volume matrix corresponds to the one or more three-dimensional A-line signals;
determine whether to receive a request to, or to give a user a choice to, increase or decrease the angle interval (AN) of an OCT image from the default angle interval;
in an event that it is determined to receive an increase or decrease request to, or to let the user change, the angle interval (AN), then calculate a number of A-lines (NA) to be NA=360/AN, or, in an event that it is determined to not receive an increase or decrease request, or to not let the user change, the angle interval (AN), then set the NA to be NA=8;
extract NA equally spaced and perpendicular to catheter or probe cross-section(s) of or from the 3D A-line volume;
detect a border or borders of the A-line cross-section(s) and/or perform segmentation procedure(s) of the 3D A-line cross-section(s);
determine whether to manually or automatically correct the detected border or borders of the vessel lumen and/or of the 3D A-line cross-section(s), and in an event that it is determined to manually or automatically correct the detected border or borders, then apply a global correction method or methods to define a new curve for the cross sectional A-line border or borders;
translate the detected border(s) of the A-line cross-section(s) to frame points and linearly interpolate the remaining points of the lumen;
calculate a distance to or of each A-line from the catheter or probe to the lumen border or borders;
transform the 2D A-line frames and lumen border or borders to OCT frames, or to frames of another set or predetermined imaging modality, or transform from A-lines to Cartesian coordinates superimposed over their corresponding OCT images; and
determine whether to perform the global correction method or methods or to perform another global correction method or methods, and in an event that it is determined to perform the global correction method or methods or to perform another global correction method or methods, then apply the global correction method or methods or the another global correction method or methods to define a new curve or curves and complete the transformation.

4. A non-transitory computer-readable storage medium storing at least one program for causing a computer to execute a method, the method comprising:
detecting a vessel lumen border or borders using an intravascular imaging signal;
calculating distance from the lumen border or borders to a catheter or probe based on one or more three-dimensional A-line signals;
depicting the lumen border or borders in each two-dimensional (2D) Optical Coherence Tomography (OCT) frame allowing for a global correction;
allowing detection of the vessel lumen borders in all data for a pullback; and
allowing for a more detailed detection in a case where an angle interval (AN) is specified that is smaller or larger than a default angle interval.

5. The non-transitory computer-readable storage medium of claim 4, wherein the method further comprises:
obtaining or receiving two-dimensional (2D) A-lines;

constructing a 3D A-line volume matrix from the 2D A-lines, where the 3D A-line volume matrix corresponds to the one or more three-dimensional A-line signals;

determining whether to receive a request to, or to give a user a choice to, increase or decrease the angle interval (AN) of an OCT image from the default angle interval;

in an event that it is determined to receive an increase or decrease request to, or to let the user change, the angle interval (AN), then calculating a number of A-lines (NA) to be NA=360/AN, or, in an event that it is determined to not receive an increase or decrease request, or to not let the user change, the angle interval (AN), then setting the NA to be NA=8;

extracting NA equally spaced and perpendicular to catheter or probe cross-section(s) of or from the 3D A-line volume;

detecting a border or borders of the A-line cross-section(s) and/or performing segmentation procedure(s) of the 3D A-line cross-section(s);

determining whether to manually or automatically correct the detected border or borders of the vessel lumen and/or of the 3D A-line cross-section(s), and in an event that it is determined to manually or automatically correct the detected border or borders, then applying a global correction method or methods to define a new curve for the cross sectional A-line border or borders;

translating the detected border(s) of the A-line cross-section(s) to frame points and linearly interpolating the remaining points of the lumen;

calculating a distance to or of each A-line from the catheter or probe to the lumen border or borders;

transforming the 2D A-line frames and lumen border or borders to OCT frames, or to frames of another set or predetermined imaging modality, or transforming from A-lines to Cartesian coordinates superimposed over their corresponding OCT images; and determining whether to perform the global correction method or methods or to perform another global correction method or methods, and in an event that it is determined to perform the global correction method or methods or to perform another global correction method or methods, then applying the global correction method or methods or the another global correction method or methods to define a new curve or curves, and completing the transforming.

6. A method comprising:
detecting a vessel lumen border or borders using an intravascular imaging signal;
calculating distance from the lumen border or borders to a catheter or probe based on one or more three-dimensional A-line signals;
depicting the lumen border or borders in each two-dimensional (2D) Optical Coherence Tomography (OCT) frame allowing for a global correction;
allowing detection of the vessel lumen borders in all data for a pullback; and
allowing for a more detailed detection in a case where an angle interval (AN) is specified that is smaller or larger than a default angle interval.

7. The method of claim 6, further comprising:
obtaining or receiving two-dimensional (2D) A-lines;
constructing a 3D A-line volume matrix from the 2D A-lines, where the 3D A-line volume matrix corresponds to the one or more three-dimensional A-line signals;

determining whether to receive a request to, or to give a user a choice to, increase or decrease the angle interval (AN) of an OCT image from the default angle interval;

in an event that it is determined to receive an increase or decrease request to, or to let the user change, the angle interval (AN), then calculating a number of A-lines (NA) to be NA=360/AN, or, in an event that it is determined to not receive an increase or decrease request, or to not let the user change, the angle interval (AN), then setting the NA to be NA=8;

extracting NA equally spaced and perpendicular to catheter or probe cross-section(s) of or from the 3D A-line volume;

detecting a border or borders of the A-line cross-section(s) and/or performing segmentation procedure(s) of the 3D A-line cross-section(s);

determining whether to manually or automatically correct the detected border or borders of the vessel lumen and/or of the 3D A-line cross-section(s), and in an event that it is determined to manually or automatically correct the detected border or borders, then applying a global correction method or methods to define a new curve for the cross sectional A-line border or borders;

translating the detected border(s) of the A-line cross-section(s) to frame points and linearly interpolating the remaining points of the lumen;

calculating a distance to or of each A-line from the catheter or probe to the lumen border or borders;

transforming the 2D A-line frames and lumen border or borders to OCT frames, or to frames of another set or predetermined imaging modality, or transforming from A-lines to Cartesian coordinates superimposed over their corresponding OCT images; and determining whether to perform the global correction method or methods or to perform another global correction method or methods, and in an event that it is determined to perform the global correction method or methods or to perform another global correction method or methods, then applying the global correction method or methods or the another global correction method or methods to define a new curve or curves, and completing the transforming.

8. The method of claim 7, wherein one or more of the following:
(i) the two-dimensional (2D) A-lines are sequential blocks of 2D A-lines;
(ii) the default angle interval is set to 45°;
(iii) the smaller the NA is, the more precise the A-line distance is; and/or
(iv) one or more of the OCT images or images of another imaging modality have or include one or more of the following: residual blood, side branches, regular shaped vessel, and/or stented and poor flashing areas.

9. The method of claim 7, wherein one or more of the following:
(i) the constructing of the 3D A-lines volume step achieves faster processing;
(ii) the constructing of the 3D A-lines volume step achieves faster processing compared to constructing an OCT frame volume; and/or
(iii) the constructing of the 3D A-lines volume step achieves faster processing since the method does not need to perform A-line transformation to Cartesian coordinates.

10. The method of claim 7, wherein one or more of the following:

(i) the detecting of the border or borders of the A-line cross-section(s) and/or performing segmentation procedure(s) of the 3D A-line cross-section(s) step is performed automatically;
(ii) the detecting of the border or borders of the A-line cross-section(s) and/or performing segmentation procedure(s) of the 3D A-line cross-section(s) step is more precise since less variance is in the 3D A-line cross-section or cross-sections than a 2D OCT cross-section;
(iii) the detecting of the border or borders step may include one or more of the following:
   (a) applying bilateral filtering and deleting the catheter or probe from an image or images;
   (b) applying Otsu's automatic thresholding;
   (c) applying a filtering technique and/or applying automatic thresholding;
   (d) smoothing the segmented images by deleting objects or small objects which correspond to image artifacts;
   (e) scanning the image from one portion of the image to another portion of the image, storing the first non-zero pixel and, in a case where the y coordinate of the first $(x_1,y_1)$ and last $(x_{end},y_{end})$ detected point differ from the first $(c_1)$ and last $(c_{end})$ column of the image, respectively, then adding as first point: $(x_1,c_1)$ and as last point: $(x_1,c_{end})$; and/or
   (f) connecting the detected non-zero pixel using a linear interpolation function;
(iv) the bilateral filter for an image H, and a window mask W is defined as:

$$I'(x) = \frac{1}{W_p}\sum_{x_i \in W} I(x_i) f_r(\|I(x_i) - I(x)\|) g_s(\|x_i - x\|),$$

having a normalization factor $W_p$:
$W_p = \Sigma_{x_i \in W} f_r(\|I(x_i)-I(x)\|) g_s(\|x_i-x\|)$, where x are the coordinates of a central pixel of the mask and the parameters $f_r$ and $g_s$ are the Gaussian kernel for smoothing differences in intensities and the spatial Gaussian kernel for smoothing differences in coordinates;
(v) to automatically threshold the 3D A-line cross-section(s) images, a threshold $Thr_{otsu}$ for the image I' is calculated using the Otsu's method, and the pixels of the image I' that are smaller than $Thr_{otsu}$ are set to a zero value such that a result is a binary image with the arterial wall represented by the non-zero objects;
(vi) the 3D A-line cross-section(s) images are automatically thresholded; and/or
(vii) the method further comprises detecting the objects that are smaller than 3% of the whole image to ensure that only the objects that correspond to the wall area are used to detect the border or borders.

11. The method of claim 7, wherein one or more of the following:
(i) the extracting NA equally spaced and perpendicular to the catheter or probe cross-section(s) of or from the 3D A-line volume step operates to increase, or to allow the user to increase, the segmentation accuracy by choosing or selecting more cross-section(s) such that a detail of the detection may be chosen automatically or manually by the user;
(ii) the applying of the global correction step operates to correct, or to allow the user to correct, either the border detection or the lumen detection;
(iii) the applying of the global correction step operates to correct, or to allow the user to correct, either the border detection or the lumen detection via a drag and drop global correction feature or features, and/or pre and post frames of the correct frame is corrected automatically or manually;
(iv) the translating the detected border(s) of the A-line cross-section(s) to frame points and linearly interpolating the remaining points of the lumen step includes A-line distance calculations such that an accuracy of the calculations or processing is improved and computational time is decreased; and/or
(v) the translating the detected border(s) of the A-line cross-section(s) to frame points and linearly interpolating the remaining points of the lumen step includes A-line distance calculations without any transformation from Cartesian to polar coordinates, such that an accuracy of the calculations or processing is improved and computational time is decreased.

12. The method of claim 7, further comprising one or more of the following: (i) preparing or determining a final lumen border or borders; and/or (ii) spinning around the catheter or probe while being simultaneously pullbacked to collect reflected optical signals that define the A-lines.

13. The method of claim 12, wherein one or more of the following:
(i) each group of A-lines represent a full spin of the catheter or probe and correspond to a cross-section of an artery;
(ii) one or more groups of A-lines are transformed to Cartesian coordinates; and/or
(iii) for each A-line, a reflected near infrared autofluorescence light (NIRAF) is collected and/or stored in corresponding to the A-lines.

14. The method of claim 7, wherein the catheter or probe involves Optical Coherence Tomography (OCT) and/or near infrared autofluorescence light (NIRAF) imaging; and
the method further includes applying a correction step to a NIRAF signal to provide a more robust NIRAF value estimation based on a distance between the catheter or probe and a target object or target lesion or based on a distance between the catheter or probe and the lumen border or borders of each A-line.

15. The method of claim 14, wherein one or more of the following:
(i) in a case where the NIRAF signal is provided simultaneously with an OCT image, both the lumen to catheter or probe distance step(s) and the correction step(s) are applied in real time; and/or
(ii) image construction and/or reconstruction includes:
   (a) importing A-lines and corresponding NIRAF values from an OCT-NIRAF apparatus or system;
   (b) correcting the NIRAF values according to a distance of the catheter or probe from the lumen border or borders; and
   (c) performing image processing, and/or performing image processing include at least: transforming the A-lines of each frame to 2D OCT images and transforming the corrected NIRAF signal to an overlaid ring around OCT.

16. The method of claim 7, wherein one or more of the following:
(i) the constructing of the 3D A-line volume matrix from the 2D A-lines step includes storing each block of A-lines A×D where A is the number of A-lines and D is the A-line depth and each block corresponds to an OCT image, to a 3D matrix, which forms the 3D A-line volume matrix, A×D×L, where L is the number of the pullback frames;

(ii) in a case where an error is created in the border or borders detection step, the created error is corrected locally or globally, and the number of the detected A-line points is reduced to X % where a Basis spline (B-spline) interpolation is applied to the other 100−X % of the points;

(iii) the method further comprises displaying a reduced points view and a spline view that operates to allow the user to visually observe any border inaccuracy or inaccuracies in the spline view and then select the corresponding points view, which opens on or in a separate window to allow the user to drag and drop any point, and to allow the user to click a create spline button to generate and display a new spline in the spline view;

(iv) the method further comprises displaying a reduced points view and a spline view that operates to allow the user to visually observe any border inaccuracy or inaccuracies in the spline view and then select the corresponding points view, which opens on or in a separate window to allow the user to drag and drop any point, and to allow the user to click a create spline button to generate and display a new spline in the spline view, and all points before and after the any point that is dragged and dropped by the user change and move according to the new point(s) coordinates; and/or (v) in a case where an error is created in the border or borders detection step, the created error is corrected locally or globally, and the number of the detected A-line points is reduced to X % where a Basis spline (B-spline) interpolation is applied to the other 100−X % of the points, where the B-spline interpolation is a polynomial function crossing specific points or control points and has a minimal support with respect to a given smoothness, and a curve for the B-spline interpolation is defined as a linear combination of control points, wherein for $\lambda+1$ control points: $\{V\}_0^\lambda = \{V_0, V_1, \ldots, V_\lambda\}$, the B-spline defines a $\kappa+1$ number of points between the control points, called knots: $\{U\}_0^\kappa = \{U_0, U_1, \ldots, U_\kappa\}$ as: $\kappa = \lambda + \rho + 1$, and a parametric curve as: $b(U) = \Sigma_{\alpha=1}^\lambda N_{\alpha,\rho}(U) V_\alpha$, where $\rho$ is the spline degree and $N_{\alpha,\rho}$, basic B-spline function.

17. The method of claim 7, wherein one or more of the following:

(i) in the translation step, the segmented 3D A-line cross-section(s) are translated to luminal A-line points;

(ii) in the translation step, the segmented 3D A-line cross-section(s) are translated to luminal A-line points, where the translation of the segmented 3D A-line cross-section(s) to luminal A-line points is based on the following:

(a) each 3D A-line cross-section(s) image corresponds to a specific point of the 2D A-line frames;

(b) each column of a 3D A-line cross-section(s) image corresponds to one of the L number of frames: column 1-frame 1, column 2-frame 2, . . . column L-frame L; and (c) each point of the detected border line in each 3D A-line cross-section corresponds to a specific point within the depth D of each 2D A-line frame;

(iii) for each 2D A-line frame, NA lumen points, where the default NA=8, are detected which correspond to NA columns of the image: 1, A/(NA−1), A×2/(NA−1), A×3/(NA−1), A×4/(NA−1), A×5/(NA−1), A×6/(NA−1), and A×7/(NA−1); and/or (iv) to detect the remaining lumen points, a linear interpolation is performed, wherein, for a pair of points $(x_a, y_a)$, $(x_b, y_b)$, their linearly interpolated point (x,y) of a known x is calculated as:

$$y = y_a + (y_b - y_a)\frac{x - x_a}{x_b - x_a}.$$

18. The method of claim 7, wherein the calculating step further includes, for each A-line, measuring the number of pixels from the lumen border or borders to the catheter or probe border, which is a known distance, and multiplying the measured number of pixels to the pixel spacing distance in order to estimate the distance.

19. The method of claim 7, wherein the transformation step further includes translating each of the detected lumen 2D A-line points and the 2D A-line images to Cartesian coordinates: $(r,\theta) \to i,j$, where r represents the range dimension, $\theta$ the acquisition angle, $i = r \cos\theta$ and $j = r \sin\theta$.

20. The method of claim 7, wherein the global correction(s) may include dragging and dropping the lumen border, wherein the NA points are automatically recalculated and move a spline of the 2D A-line cross-sections, correcting globally the lumen border or borders in all the image frames.

* * * * *